US011101024B2

(12) United States Patent
D'Souza et al.

(10) Patent No.: US 11,101,024 B2
(45) Date of Patent: *Aug. 24, 2021

(54) MEDICAL CODING SYSTEM WITH CDI CLARIFICATION REQUEST NOTIFICATION

(71) Applicant: Nuance Communications, Inc., Burlington, MA (US)

(72) Inventors: Howard D'Souza, Chantilly, VA (US); Debjani Sarkar, Herndon, VA (US)

(73) Assignee: Nuance Communications, Inc., Burlington, MA (US)

(*) Notice: Subject to any disclaimer, the term of this patent is extended or adjusted under 35 U.S.C. 154(b) by 96 days.

This patent is subject to a terminal disclaimer.

(21) Appl. No.: 16/502,626

(22) Filed: Jul. 3, 2019

(65) Prior Publication Data

US 2020/0126643 A1    Apr. 23, 2020

Related U.S. Application Data

(63) Continuation of application No. 14/296,274, filed on Jun. 4, 2014, now Pat. No. 10,373,711.

(51) Int. Cl.
*G16H 10/60* (2018.01)
*G16H 15/00* (2018.01)
*G06Q 30/02* (2012.01)
*G06Q 30/04* (2012.01)

(52) U.S. Cl.
CPC ......... *G16H 10/60* (2018.01); *G06Q 30/0283* (2013.01); *G06Q 30/04* (2013.01); *G16H 15/00* (2018.01)

(58) Field of Classification Search
None
See application file for complete search history.

(56) References Cited

U.S. PATENT DOCUMENTS

| | | | |
|---|---|---|---|
| 4,696,039 | A | 9/1987 | Doddington |
| 5,031,113 | A | 7/1991 | Hollerbauer |
| 5,051,924 | A | 9/1991 | Bergeron et al. |

(Continued)

FOREIGN PATENT DOCUMENTS

| | | |
|---|---|---|
| DE | 19533541 C1 | 3/1997 |
| DE | 102007021284 A1 | 11/2008 |

(Continued)

OTHER PUBLICATIONS

Ferrao et al, Clinical Coding Support Based on Structured Data Stored in Electronic Health Records, 2012, IEEE International Conference on Bioinformatics and Biomedicine Workshops, Oct. 2012, pp. 790-797 (Year: 2012).*

(Continued)

*Primary Examiner* — Gregory Lultschik
(74) *Attorney, Agent, or Firm* — Wolf, Greenfield & Sacks, P.C.

(57) ABSTRACT

Techniques are provided whereby a clarification request may be generated with a clinical documentation improvement (CDI) system for resolution by a clinician, and notification of the clarification request may be transmitted to a medical coding system. At a medical coding system, notification may be received of a clarification request generated at a CDI system for resolution by a clinician. In some embodiments, the medical coding system may be a computer-assisted coding (CAC) system.

20 Claims, 19 Drawing Sheets

(56) References Cited

U.S. PATENT DOCUMENTS

| | | |
|---|---|---|
| 5,307,262 A | 4/1994 | Ertel |
| 5,680,511 A | 10/1997 | Baker et al. |
| 5,758,322 A | 5/1998 | Rongley |
| 5,787,394 A | 7/1998 | Bahl et al. |
| 5,909,667 A | 6/1999 | Leontiades et al. |
| 5,924,074 A | 7/1999 | Evans |
| 5,999,896 A | 12/1999 | Richardson et al. |
| 6,003,002 A | 12/1999 | Netsch |
| 6,073,101 A | 6/2000 | Maes |
| 6,173,259 B1 | 1/2001 | Bijl et al. |
| 6,212,498 B1 | 4/2001 | Sherwood et al. |
| 6,292,771 B1 | 9/2001 | Haug et al. |
| 6,360,237 B1 | 3/2002 | Schulz et al. |
| 6,366,882 B1 | 4/2002 | Bijl et al. |
| 6,418,410 B1 | 7/2002 | Nassiff et al. |
| 6,434,547 B1 | 8/2002 | Mishelevich et al. |
| 6,463,413 B1 | 10/2002 | Applebaum et al. |
| 6,487,530 B1 | 11/2002 | Lin et al. |
| 6,519,561 B1 | 2/2003 | Farrell et al. |
| 6,567,778 B1 | 5/2003 | Chao Chang et al. |
| 6,813,603 B1 | 11/2004 | Groner et al. |
| 6,915,254 B1 | 7/2005 | Heinze et al. |
| 7,233,938 B2 | 6/2007 | Carus et al. |
| 7,383,172 B1 | 6/2008 | Jamieson |
| 7,493,253 B1 | 2/2009 | Ceusters et al. |
| 7,610,192 B1 | 10/2009 | Jamieson |
| 7,983,922 B2 | 7/2011 | Neusinger et al. |
| 8,204,756 B2 | 6/2012 | Kim et al. |
| 8,208,641 B2 | 6/2012 | Oh et al. |
| 8,326,653 B2 | 12/2012 | Gottlieb et al. |
| 8,612,261 B1 | 12/2013 | Swanson et al. |
| 8,694,335 B2 | 4/2014 | Yegnanarayanan |
| 8,756,079 B2 | 6/2014 | Yegnanarayanan |
| 8,943,437 B2 | 1/2015 | Meurs |
| 9,324,321 B2 | 4/2016 | Xue et al. |
| 9,478,218 B2 | 10/2016 | Shu |
| 9,715,576 B2 | 7/2017 | Hayter, II |
| 9,892,734 B2 | 2/2018 | Koll et al. |
| 10,319,004 B2 | 6/2019 | Reiser et al. |
| 10,331,763 B2 | 6/2019 | Subramanian et al. |
| 10,366,424 B2 | 7/2019 | Spitznagel et al. |
| 10,366,687 B2 | 7/2019 | Zhan et al. |
| 10,373,711 B2 | 8/2019 | D'Souza et al. |
| 10,754,925 B2 | 8/2020 | D'Souza et al. |
| 10,902,845 B2 | 1/2021 | Zhan et al. |
| 2003/0115083 A1 | 6/2003 | Masarie, Jr. et al. |
| 2003/0163461 A1 | 8/2003 | Gudbjartsson et al. |
| 2003/0212544 A1 | 11/2003 | Acero et al. |
| 2004/0044952 A1 | 3/2004 | Jiang et al. |
| 2004/0073458 A1 | 4/2004 | Jensen |
| 2004/0220831 A1 | 11/2004 | Fabricant |
| 2005/0033574 A1 | 2/2005 | Kim et al. |
| 2005/0228815 A1 | 10/2005 | Carus et al. |
| 2005/0240439 A1 | 10/2005 | Covit et al. |
| 2006/0136197 A1* | 6/2006 | Oon .................. G06F 40/186 704/9 |
| 2006/0190300 A1 | 8/2006 | Drucker |
| 2006/0242190 A1 | 10/2006 | Wnek |
| 2007/0033026 A1 | 2/2007 | Bartosik et al. |
| 2007/0050187 A1 | 3/2007 | Cox |
| 2007/0088564 A1 | 4/2007 | March et al. |
| 2007/0208567 A1 | 9/2007 | Amento et al. |
| 2008/0002842 A1 | 1/2008 | Neusinger et al. |
| 2008/0004505 A1 | 1/2008 | Kapit et al. |
| 2008/0147436 A1 | 6/2008 | Ohlsson |
| 2008/0222734 A1 | 9/2008 | Redlich et al. |
| 2008/0255835 A1 | 10/2008 | Ollason et al. |
| 2008/0262853 A1 | 10/2008 | Jung et al. |
| 2008/0270120 A1 | 10/2008 | Pestian et al. |
| 2009/0157411 A1 | 6/2009 | Kim et al. |
| 2009/0210238 A1 | 8/2009 | Kim et al. |
| 2009/0216528 A1 | 8/2009 | Gemello et al. |
| 2009/0281839 A1 | 11/2009 | Lynn et al. |
| 2009/0326958 A1 | 12/2009 | Kim et al. |
| 2010/0023319 A1 | 1/2010 | Bikel et al. |
| 2010/0049756 A1 | 2/2010 | Chemitiganti et al. |
| 2010/0076772 A1 | 3/2010 | Kim et al. |
| 2010/0076774 A1 | 3/2010 | Breebaart |
| 2010/0161316 A1 | 6/2010 | Haug |
| 2010/0198602 A1 | 8/2010 | Oh et al. |
| 2010/0198755 A1 | 8/2010 | Soll et al. |
| 2010/0250236 A1 | 9/2010 | Jagannathan et al. |
| 2010/0274584 A1 | 10/2010 | Kim |
| 2011/0040576 A1 | 2/2011 | Madan et al. |
| 2012/0078763 A1 | 3/2012 | Koll et al. |
| 2012/0089629 A1 | 4/2012 | Koll et al. |
| 2012/0109641 A1 | 5/2012 | Boone et al. |
| 2012/0215559 A1 | 8/2012 | Flanagan et al. |
| 2012/0245961 A1 | 9/2012 | Yegnanarayanan |
| 2013/0035961 A1 | 2/2013 | Yegnanarayanan |
| 2013/0041685 A1 | 2/2013 | Yegnanarayanan |
| 2013/0067319 A1 | 3/2013 | Olszewski et al. |
| 2013/0073301 A1 | 3/2013 | Rao et al. |
| 2013/0080187 A1* | 3/2013 | Bacon .................. G16H 15/00 705/3 |
| 2013/0246098 A1 | 9/2013 | Habboush et al. |
| 2013/0297347 A1 | 11/2013 | Cardoza et al. |
| 2013/0297348 A1 | 11/2013 | Cardoza et al. |
| 2013/0318076 A1 | 11/2013 | Chiticariu et al. |
| 2014/0164023 A1 | 6/2014 | Yegnanarayanan |
| 2014/0244257 A1 | 8/2014 | Colibro et al. |
| 2014/0257803 A1 | 9/2014 | Yu et al. |
| 2014/0278460 A1 | 9/2014 | Dart et al. |
| 2014/0280353 A1 | 9/2014 | Delaney et al. |
| 2014/0343957 A1 | 11/2014 | Dejori |
| 2014/0372142 A1 | 12/2014 | Reddy |
| 2014/0372147 A1* | 12/2014 | White ................ G06F 16/2455 705/3 |
| 2014/0372216 A1 | 12/2014 | Nath et al. |
| 2015/0039299 A1 | 2/2015 | Weinstein et al. |
| 2015/0039301 A1 | 2/2015 | Senior et al. |
| 2015/0039344 A1 | 2/2015 | Kinney |
| 2015/0046178 A1 | 2/2015 | Jindal |
| 2015/0066974 A1 | 3/2015 | Winn |
| 2015/0095016 A1 | 4/2015 | Karres et al. |
| 2015/0112680 A1 | 4/2015 | Lu |
| 2015/0134361 A1 | 5/2015 | Molenda |
| 2015/0142473 A1 | 5/2015 | Sethumadhavan et al. |
| 2015/0149165 A1 | 5/2015 | Saon |
| 2015/0161522 A1 | 6/2015 | Saon et al. |
| 2015/0161995 A1 | 6/2015 | Sainath et al. |
| 2015/0178874 A1 | 6/2015 | Harris et al. |
| 2015/0356057 A1 | 12/2015 | Subramanian et al. |
| 2015/0356198 A1 | 12/2015 | D'Souza et al. |
| 2015/0356246 A1 | 12/2015 | D'Souza et al. |
| 2015/0356260 A1 | 12/2015 | D'Souza et al. |
| 2015/0356458 A1 | 12/2015 | Berengueres et al. |
| 2015/0356646 A1 | 12/2015 | Spitznagel et al. |
| 2015/0356647 A1 | 12/2015 | Reiser et al. |
| 2015/0371634 A1 | 12/2015 | Kim |
| 2015/0379241 A1 | 12/2015 | Furst et al. |
| 2016/0012186 A1* | 1/2016 | Zasowski ............ G16H 40/67 705/3 |
| 2016/0085743 A1 | 3/2016 | Haley |
| 2016/0260428 A1 | 9/2016 | Matsuda et al. |
| 2016/0300034 A1 | 10/2016 | Huddar et al. |
| 2016/0364532 A1 | 12/2016 | Honeycutt et al. |
| 2017/0039326 A1 | 2/2017 | Stankiewicz et al. |
| 2017/0061085 A1 | 3/2017 | Nossal et al. |
| 2017/0104785 A1 | 4/2017 | Stolfo et al. |
| 2017/0116373 A1 | 4/2017 | Ginsburg et al. |
| 2017/0169815 A1 | 6/2017 | Zhan et al. |
| 2017/0300635 A1 | 10/2017 | Ganesan et al. |
| 2017/0323060 A1 | 11/2017 | D'Souza et al. |
| 2017/0323061 A1 | 11/2017 | D'Souza et al. |
| 2018/0032678 A1 | 2/2018 | Dandala et al. |
| 2018/0032679 A1 | 2/2018 | Dandala et al. |
| 2018/0052961 A1 | 2/2018 | Shrivastava et al. |
| 2018/0081859 A1 | 3/2018 | Snider et al. |
| 2018/0089373 A1 | 3/2018 | Matsuguchi et al. |
| 2018/0090142 A1 | 3/2018 | Li et al. |
| 2018/0119137 A1 | 5/2018 | Matsuguchi et al. |
| 2018/0373844 A1 | 12/2018 | Ferrandez-Escamez et al. |
| 2019/0027235 A1 | 1/2019 | Ferrandez-Escamez et al. |

(56) References Cited

U.S. PATENT DOCUMENTS

| | | |
|---|---|---|
| 2019/0080450 A1 | 3/2019 | Arar et al. |
| 2019/0130073 A1 | 5/2019 | Sun et al. |
| 2019/0325859 A1 | 10/2019 | Zhan et al. |
| 2019/0385202 A1 | 12/2019 | Reiser et al. |
| 2020/0126130 A1 | 4/2020 | Spitznagel et al. |

FOREIGN PATENT DOCUMENTS

| | | |
|---|---|---|
| EP | 1 361 522 A2 | 11/2003 |
| WO | WO 98/19253 A1 | 5/1998 |
| WO | WO 2013/133891 A1 | 9/2013 |
| WO | WO 2015/084615 A1 | 6/2015 |

OTHER PUBLICATIONS

U.S. Appl. No. 14/296,214, filed Jun. 4, 2014, Spitznagel et al.
U.S. Appl. No. 16/526,443, filed Jul. 30, 2019, Spitznagel et al.
U.S. Appl. No. 14/296,249, filed Jun. 4, 2014, Subramanian et al.
U.S. Appl. No. 16/402,867, filed May 3, 2019, Subramanian et al.
U.S. Appl. No. 14/296,256, filed Jun. 4, 2014, D'Souza et al.
U.S. Appl. No. 14/296,274, filed Jun. 4, 2014, D'Souza et al.
U.S. Appl. No. 14/296,295, filed Jun. 4, 2014, D'Souza et al.
U.S. Appl. No. 15/977,451, filed May 11, 2018, D'Souza et al.
U.S. Appl. No. 14/296,303, filed Jun. 4, 2014, Reiser et al.
U.S. Appl. No. 16/395,954, filed Apr. 26, 2019, Reiser et al.
U.S. Appl. No. 14/965,637, filed Dec. 10, 2015, Zhan et al.
U.S. Appl. No. 16/459,335, filed Jul. 1, 2019, Zhan et al.
U.S. Appl. No. 15/372,338, filed Dec. 7, 2016, D'Souza et al.
U.S. Appl. No. 15/366,905, filed Dec. 1, 2016, D'Souza et al.
U.S. Appl. No. 15/632,152, filed Jun. 23, 2017, Oscar et al.
U.S. Appl. No. 15/796,658, filed Oct. 27, 2017, Sun et al.
U.S. Appl. No. 15/710,319, filed Sep. 20, 2017, Snider et al.
PCT/US2015/033642, Sep. 9, 2015, International Search Report and Written Opinion.
PCT/US2015/033130, Aug. 6, 2015, International Search Report and Written Opinion.
PCT/US2015/033648, Aug. 11, 2015, International Search Report and Written Opinion.
PCT/US2016/061326, Feb. 21, 2017, International Search Report and Written Opinion.
PCT/US2016/061326, Jun. 21, 2018, International Preliminary Report on Patentability.
PCT/US2017/052542, Dec. 14, 2017, International Search Report and Written Opinion.
PCT/US2017/052542, Apr. 4, 2019, International Preliminary Report on Patentability.
U.S. Appl. No. 16/026,641, filed Jul. 3, 2018, Ferrandez-Escamez et al.
International Search Report and Written Opinion for International Application No. PCT/US2015/033642 dated Sep. 9, 2015.
International Search Report and Written Opinion for International Application No. PCT/US2015/033130 dated Aug. 6, 2015.
International Search Report and Written Opinion for International Application No. PCT/US2015/033648 dated Aug. 11, 2015.
International Search Report and Written Opinion for International Application No. PCT/US2016/061326 dated Feb. 21, 2017.
International Preliminary Report on Patentability for International Application No. PCT/US2016/061326 dated Jun. 21, 2018.
International Search Report and Written Opinion for International Application No. PCT/US2017/052542 dated Dec. 14, 2017.
International Preliminary Report on Patentability for International Application No. PCT/US2017/052542 dated Apr. 4, 2019.
[No Author Listed], Asthma specificity and tobacco use highlight ICD-10-CM respiratory changes. HCPro. JustCoding News. 2014. 4 pages.
[No Author Listed], Chronic lower respiratory diseases J40-J47. 2015 ICD-10-CM Diagnosis Codes. ICD10Data.com 2015. 6 pages.
[No Author Listed], Injury, poisoning and certain other consequences of external causes S00-T88. 2015 ICD-10-CM Diagnosis Codes. ICD10Data.com 2015. 35 pages.
Abrash et al., Connectionist Speaker Normalization and Adaptation. Proc. Eurospeech'95, 1995. 4 pages.
Aronow et al., Ad Hoc Classification of Radiology Reports. Journal of the American Medical Informatics Association. 1999;6(5):393-411.
Bateman et al., The Quest for the Last 5%: Interfaces for Correcting Real-Time Speech-Generated Subtitles. Interactive Posters. CHI 2000. 2 pages.
Birnbaum et al., Report: A Voice Password System for Access Security. AT&T Technical Journal. 1986. 7 pages.
Bisani et al., Automatic Editing in a Back-End Speech-to-Text System. Proceedings of ACL-08: HLT. 2008:114-20.
Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine LearningMethods, Bonn, Germany, (2005).
Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Ferrao et al., Clinical Coding Support Based on Structured Data Stored in Electronic Health Records. IEEE International Conference on Bioinformatics and Biomedicine Workshops. 2012. 790-7.
Florian et al., "A Statistical Model for Multilingual Entity Detection and Tracking," Proceedings of the Human Language Technologies Conference 2004 (HLT-NAACL'04), (2004).
Gemello et al., Linear hidden transformations for adaptation of hybrid ANN/HMM Models. Speech Communication. 2007;49:827-35.
Gomez-Perez et al., "An overview of methods and tools for ontology learning from texts," Knowledge Engineering Review 19:3 p. 187-212, 2004.
Heng-Hsou et al., An Event-Driven and Ontology-Based Approach for the Delivery and Information Extraction of E-mails. IEEE. 2000. 103-9.
Hewitt et al., Real-Time Speech-Generated Subtitles: Problems and Solutions. ISCA Archive. 6th International Conference on Spoken Language Processing (ICSLP 2000). 2000. 5 pages.
Mendonca et al., Extracting information on pneumonia in infants using natural language processing of radiology reports. Journal of Biomedical Informatics. 2005;38:314-21.
Naik, Speaker Verification: A Tutorial. IEEE Communications Magazine. 1990:42-8.
Newman et al., Speaker Verifcation Through Large Vocabulary Continuous Speech Recognition. Dragon Systems, Inc. 1996. 4 pages.
Omar, Fast Approximate I-Vector Estimation Using PCA. Proc. ICASSP. IEEE, 2015;4495-9.
Rosenberg, Evaluation of an Automatic Speaker-Verification System Over Telephone Lines. The Bell System Technical Journal. 1976;55(6):723-44.
Salton et al., "A Vector Space Model for Automatic Indexing," Communications of the ACM, vol. 18, No. 11, Nov. 1975.
Saon et al., Speaker Adaptation of Neural Network Acoustic Models Using I-Vectors. IEEE. 2013;55-9.
Senior et al., Improving DNN speaker independence with I-vector inputs. 2014 IEEE International Conference on Acoustics, Speech and Signal Processing (ICASSP), IEEE. 2014;225-9.
Shvaiko et al., Ontology Matching OM-2008. Papers from the ISWC Workshop. 2008. 271 pages.
Sistrom et al., Managing Predefined Templated and Macros for a Departmental Speech Recognition System Using Common Software. Journal of Digital Imaging. 2001;14(3):131-41.
Soderland et al., Automated Classification of Encounter Notes in a Computer Based Medical Record. MEDINFO 1995 Proceedings. 1995 IMIA. 9 pages.
Sonntag et al., A Discourse and Dialogue Infrastructure for Industrial Dissemination. German Research Center for AI (DFKI). Pro-

(56) References Cited

OTHER PUBLICATIONS ceeding IWSDS'10 Proceedings of the Second international conference on Spoken dialogue systems for ambient environments. 2010. 12 pages.

Sonntag et al., RadSpeech's Mobile Dialogue System for Radiologists. IUI'12. 2012. 2 pages.

Suhm, Multimodal Interactive Error Recovery for Non-Conversation Speech User Interfaces. Dissertation. 1998. 292 pages.

Taira et al., Automatic Structuring of Radiology Free-Text Reports. infoRAD. Radiology 2001;21:237-45.

Welty et al., "Large Scale Relation Detection," Proceedings of the NAACL HLT 2010 First International Workshop on Formalisms and Methodology for Learning by Reading, pp. 24-33, Los Angeles, California, Jun. 2010.

U.S. Appl. No. 16/928,519, filed Jul. 14, 2020, D'Souza et al.

\* cited by examiner

Patient Name [John Doe] Sex [M] Creation Date [01-18-2011]
Document Type [Discharge Summary]

Problems Medications Allergies Social History Procedures Vital Signs  Show All

300

⊟ Problems(4)

[Add Fact] — 430

| Name | Status |
|---|---|
| × Unspecified Chest Pain | active |
| × Shortness of Breath | active |
| × Unspecified Essential Hypertension | history |
| × Obesity Unspecified | history |

410

Chief complaint: Patient is presenting ~~chest pain~~ and shortness of breath.

420

Medical history: The patient is hypertensive. He is also obese.

Social history: He smokes one pack per day. Drinks occasionally.

⊟ Medications(1)

[Add Fact]

| Name | Status | Schedules |
|---|---|---|
| × | | None |

⊟ Allergies(0)

[Add Fact]

| Name | Type | Status |
|---|---|---|

230

[Save] [Dictate] [Complete] [Cancel]

Document List — 710

- History & Physical
  - 6/13/2014
- Discharge Summary — 712
  - 6/18/2014
- Emergency Room Record
  - 6/13/2014
- Consultation
  - 6/15/2014
- Progress Notes
  - 6/17/2014
- Operative Report
  - 6/13/2014

Submit — 750

Discharge Summary 6/18/2014 — 720

HISTORY OF PRESENT ILLNESS/ HOSPITAL COURSE:
The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. — 722
He was intubated and put into the ICU. The patient is doing well today. No acute symptoms. He denies any chest pain or shortness of breath. No fevers or chills.

Code List — 730

| Diagnosis | Procedure | | |
|---|---|---|---|
| | ICD9 | Description | POA — 740 |
| ☑ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Submit — 750

Document List — 710
- History & Physical
  - 6/13/2014
- Discharge Summary — 712
  - 6/15/2014
  - 6/18/2014
- Emergency Room Record
  - 6/13/2014
- Consultation
  - 6/15/2014
- Progress Notes
  - 6/17/2014
- Operative Report
  - 6/13/2014

Discharge Summary 6/18/2014 — 720

HISTORY OF PRESENT ILLNESS/
HOSPITAL COURSE:
The patient is a 63-year old male with a history of multiple medical problems. He was originally admitted on June 13 when he was found unresponsive at home. Left heart catheterization showed normal coronaries, and no pulmonary embolism appreciated on pulmonary angiogram. Bilateral infiltrative changes suggested pneumonia. Patient was treated for that and sent to rehab unit. He developed respiratory distress and was readmitted to the hospital with hypercapnic respiratory failure. He was intubated and put into the ICU. The patient is doing well today. No acute symptoms. He denies any chest pain or shortness of breath. No fevers or chills.

Code List — 730

| | Diagnosis | Procedure | |
|---|---|---|---|
| | ICD9 | Description | POA — 740 |
| ☑ | 518.81 | Acute Respiratory Failure | |
| ○ | 287.5 | Thrombocytopenia | |
| ○ | 338 | ▷ Show Highlights<br>Accept<br>Reject<br>Replace<br>Link Text<br>Unlink Text | |
| ○ | 571 | | |
| ○ | 303 | NEC/NOS | nce |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List — 750

- History & Physical
  6/13/2014
- Discharge Summary — 712
  6/15/2014
- Emergency Room Record
  6/13/2014
- Consultation
  6/15/2014
- Progress Notes
  6/17/2014
- Operative Report
  6/13/2014

Submit

710

720

Discharge Summary 6/18/2014

DISCHARGE DIAGNOSES:
1. Acute hypercapnic respiratory failure.
2. Thrombocytopenia. — 726
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found

730

Code List — 740

| Diagnosis | Procedure | | |
|---|---|---|---|
| | ICD9 | Description | POA |
| ☑ | 518.81 | Acute Respiratory Failure | |
| ○ | 287.5 | Thrombocytopenia NOS | |
| ○ | 338.4 | Chronic Pain Syndrome | |
| ○ | 571.5 | Cirrhosis of Liver w/o Alcohol | |
| ○ | 303.90 | Alcohol Dependence NEC/NOS | |
| ○ | 571.2 | Alcoholic Cirrhosis of Liver | |
| ○ | 428.0 | Congestive Heart Failure, Unspec | |
| ○ | 482.9 | Bacterial Pneumonia NOS | |

Document List 750

- History & Physical
  - 6/13/2014
  - 6/15/2014
- Discharge Summary — 712
  - 6/13/2014
- Emergency Room Record
  - 6/13/2014
- Consultation
  - 6/13/2014
- Progress Notes
  - 6/17/2014
- Operative Report
  - 6/13/2014

Submit

710

720

Discharge Summary 6/18/2014
DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CHF)
7. History of multilobular pseudomonas pneumonia in sacral wounds with general deconditioning, weakness and fatigue.

HISTORY OF PRESENT ILLNESS/HOSPITAL COURSE
The patient is a 63-year old male with a history of multiple medical problems. He was originally admitted on June 13 when he was found

730

Code List — 740

| Diagnosis | Procedure | | |
|---|---|---|---|
| | ICD9 | Description | POA |
| ⊘ | 518.81 | Acute Respiratory Failure | |
| ⊘ | 287.5 | Thrombocytopenia NOS | |
| ⊘ | 338.4 | Chronic Pain Syndrome | |
| ⊘ | 571.5 | Cirrhosis of Liver w/o Alcohol | |
| ⊘ | 303.90 | Alcohol Dependence NEC/NOS | |
| ⊘ | 571.2 | Alcoholic Cirrhosis of Liver | |
| ⊕ | 428.0 | Congestive Heart Failure, Unspec | |
| ⊕ | 482.1 | Pneumonia due to Pseudomonas | |
| ⊕ | 041.7 | Pseudomonas infection Site NOS | |

Document List (710)
- History & Physical
  - 6/13/2014
  - 6/15/2014
- Discharge Summary — 712
  - 6/13/2014
- Emergency Room Record
  - 6/13/2014
- Consultation
  - 6/13/2014
- Progress Notes
  - 6/17/2014
- Operative Report
  - 6/13/2014

Submit — 750

Document (720)

Discharge Summary 6/18/2014
DISCHARGE DIAGNOSES:
1. Acute hypercapnic respiratory failure.
2. Thrombocytopenia.
3. Chronic pain syndrome.
4. History of liver cirrhosis.
5. Alcoholism.
6. Congestive heart failure (CH
7. History of multilobular pseudomonas pneumonia in sacral wounds with general deconditioning, weakness and fatigue.

HISTORY OF PRESENT ILLNESS/ HOSPITAL COURSE

The patient is a 63-year old male with a history of multiple medical problems. He was originally admitted on June 13 when he was found Pop-up menu:
✓ Incorrect Code
More specific code needed
Partial Code
Negated Code
Not Billable
Payor Specific

Code List (730)

| Diagnosis | Procedure |

| | ICD9 | Description | POA |
|---|---|---|---|
| ⊘ | 518.81 | Acute Respiratory Failure | |
| ⊘ | 287.5 | Thrombocytopenia NOS | |
| ⊘ | 4 | Chronic Pain Syndrome | |
| ⊘ | 5 | Cirrhosis of liver | |
| | | Show Highlights | |
| | | Accept | |
| | | Rejected Reason | |
| ⊘ | 57 | Replace | |
| ⊘ | 42 | Link Text | |
| | | Unlink Text | |
| ⊕ | 482.1 | Pneumonia due to Pseudomonas | |
| ⊕ | 041.7 | Pseudomonas infection Site NOS | |

| Save | | |
|---|---|---|
| Code | Description | POA |
| 1. 518.81 | Acute Respiratory Failure | N |
| 2. 287.5 | Thrombocytopenia NOS | Y |
| 3. 338.4 | Chronic Pain Syndrome | Y |
| 4. 303.90 | Alcohol Dependence NEC/NOS | Y |
| 5. 571.2 | Alcoholic Cirrhosis of Liver | Y |
| 6. 428.0 | Congestive Heart Failure, Unspecified | Y |
| 7. 482.1 | Pneumonia due to Pseudomonas | Y |
| 8. 041.7 | Pseudomonas Infection Site NOS/Dis Class Elsewhere | Y |

FIG. 8

MEDICAL CODING SYSTEM WITH CDI CLARIFICATION REQUEST NOTIFICATION

CROSS-REFERENCE TO RELATED APPLICATIONS

This Application claims the benefit under 35 U.S.C. § 120 as a continuation of U.S. application Ser. No. 14/296,274, filed Jun. 4, 2014, entitled "MEDICAL CODING SYSTEM WITH CDI CLARIFICATION REQUEST NOTIFICATION," the content of which is incorporated herein by reference in its entirety.

BACKGROUND

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart", or "chart". Each patient's chart would include a stack of paper reports, such as intake forms, history and immunization records, laboratory results and clinicians' notes. Following an encounter with the patient, such as an office visit, a hospital round or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel. For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed and updated by multiple different personnel from local and remote locations through suitable user interfaces and network connections, eliminating the need to retrieve and deliver paper files from a crowded file room.

Another modern trend in healthcare management is the importance of medical coding for documentation and billing purposes. In the medical coding process, documented information regarding a patient encounter, such as the patient's diagnoses and clinical procedures performed, is classified according to one or more standardized sets of codes for reporting to various entities such as payment providers (e.g., health insurance companies that reimburse clinicians for their services). In the United States, some such standardized code systems have been adopted by the federal government, which then maintains the code sets and recommends or mandates their use for billing under programs such as Medicare.

For example, the International Classification of Diseases (ICD) numerical coding standard, developed from a European standard by the World Health Organization (WHO), was adopted in the U.S. in version ICD-9-CM (Clinically Modified). It is mandated by the Health insurance Portability and Accountability Act of 1996 (HIPAA) for use in coding patient diagnoses. The Centers for Disease Control (CDC), the National Center for Health Statistics (NCHS), and the Centers for Medicare and Medicaid Services (CMS) are the U.S. government agencies responsible for overseeing all changes and modifications to ICD-9-CM, and a new version ICD-10-CM is scheduled for adoption in 2015.

Another example of a standardized code system adopted by the U.S. government is the Current Procedural Terminology (CPT) code set, which classifies clinical procedures in five-character alphanumeric codes. The CPT code set is owned by the American Medical Association (AMA), and its use is mandated by CMS as part of the Healthcare Common Procedure Coding System (HCPCS), CPT forms HCPCS Level I, and HCPCS Level II adds codes for medical supplies, durable medical goods, non-physician healthcare services, and other healthcare services not represented in CPT. CMS maintains and distributes the HCPCS Level II codes with quarterly updates.

Conventionally, the coding of a patient encounter has been a manual process performed by a human professional, referred to as a "medical coder" or simply "coder," with expert training in medical terminology and documentation as well as the standardized code sets being used and the relevant regulations. The coder would read the available documentation from the patient encounter, such as the clinicians' narrative reports, laboratory and radiology test results, etc., and determine the appropriate codes to assign to the encounter. The coder might make use of a medical coding system, such as a software program running on suitable hardware, that would display the documents from the patient encounter for the coder to read, and allow the coder to manually input the appropriate codes into a set of fields for entry in the record. Once finalized, the set of codes entered for the patient encounter could then be sent to a payment provider, which would typically determine the level of reimbursement for the encounter according to the particular codes that were entered.

Many healthcare institutions today also have a Clinical Documentation Improvement (CDI) process in place to ensure they, have complete and accurate clinical documentation. This process is a manual process involving a trained Clinical Documentation Specialist (CDS). A CDS, also sometimes referred to as a CDI specialist, is a professional trained in reviewing clinical documentation (such as physician's notes) for completeness to ensure the proper detail exists so that the correct supporting information is included to support a given diagnosis or that the proper diagnosis is reflected in the documentation. This aids with more accurate documentation to reflect the patient diagnosis and ultimately helps feed into the process to ensure the hospital is appropriately billing and being reimbursed for the appropriate diagnosis.

When, as a result of his or her manual review of clinical documentation, a CDS identifies areas where the documentation may not provide the required information, the conventional CDI process will involve the CDS following up manually with the clinician to get the required information. Such a conventional follow-up process requires a manual action of some sort by the CDS (such as an email, a message to the clinician's inbox, or even sometimes a sticky note in the patient chart) to get the required information.

Specialized software tools have been developed that can be installed at the customer site (e.g., a hospital or clinic) to allow the CDS to review clinical documentation for completeness. The CDS will use such a tool to review the various factors reflected in the clinical documentation and ensure that the proper diagnosis based on the known information can be made. If any information required to support the clinician's diagnosis has not been documented, the CDS will manually use the tool to generate a clarification request to the clinician to get the required information to ensure the documentation reflects the diagnosis as accurately as possible. An example of such a specialized software tool for use by a CDS is the Compliant Document Management Program Guide (CDMP Guide) product offered by J. A. Thomas & Associates (JATA), a wholly owned subsidiary of Nuance Communications, Inc. ("Nuance"), of Burlington, Mass.

SUMMARY

One type of embodiment is directed to a method comprising: with a CDI system, generating a clarification request for resolution by a clinician; and transmitting to a medical coding system notification of the clarification request.

Another type of embodiment is directed to a method comprising: with a CDI system, generating a clarification request for resolution by a clinician; and transmitting a CAC system notification of the clarification request.

Another type of embodiment is directed to a method comprising: receiving, at a medical coding system, notification of a clarification request generated at a CDI system for resolution by a clinician.

Another type of embodiment is directed to a method comprising: receiving, at a CAC system, notification of a clarification request generated at a CDI system for resolution by a clinician.

Another type of embodiment is directed to at least one computer-readable storage medium storing computer-executable instructions that, when executed, perform a method comprising: receiving, at a medical coding system, notification of a clarification request generated at a CDI system for resolution by a clinician.

Another type of embodiment is directed to at least one computer-readable storage medium storing computer-executable instructions that, when executed, perform a method comprising: receiving, at a CAC system, notification of a clarification request generated at a CDI system for resolution by a clinician.

Another type of embodiment is directed to at least one computer-readable storage medium storing computer-executable instructions that, when executed, perform a method comprising: with a CDI system, generating a clarification request for resolution by a clinician; and transmitting to a medical coding system notification of the clarification request.

Another type of embodiment is directed to at least one computer-readable storage medium storing computer-executable instructions that, when executed, perform a method comprising: with a CDI system, generating a clarification request for resolution by a clinician; and transmitting to a CAC system notification of the clarification request.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a screenshot illustrating an exemplary graphical user interface for review of extracted medical facts in accordance with some embodiments;

FIGS. 3A and 3B are screenshots illustrating an exemplary display of medical facts in a user interface in accordance with some embodiments;

FIG. 4 is a screenshot illustrating an exemplary display of linkage between text and a medical fact in accordance with some embodiments;

FIG. 5 is a screenshot illustrating an exemplary interface for entering a medical fact in accordance with some embodiments;

FIGS. 7A-7G are screenshots illustrating an exemplary user interface for a computer-assisted coding (CAC) system in accordance with some embodiments;

FIG. 8 is a screenshot illustrating an exemplary code finalization screen in accordance with some embodiments;

DETAILED DESCRIPTION

Figure 1:
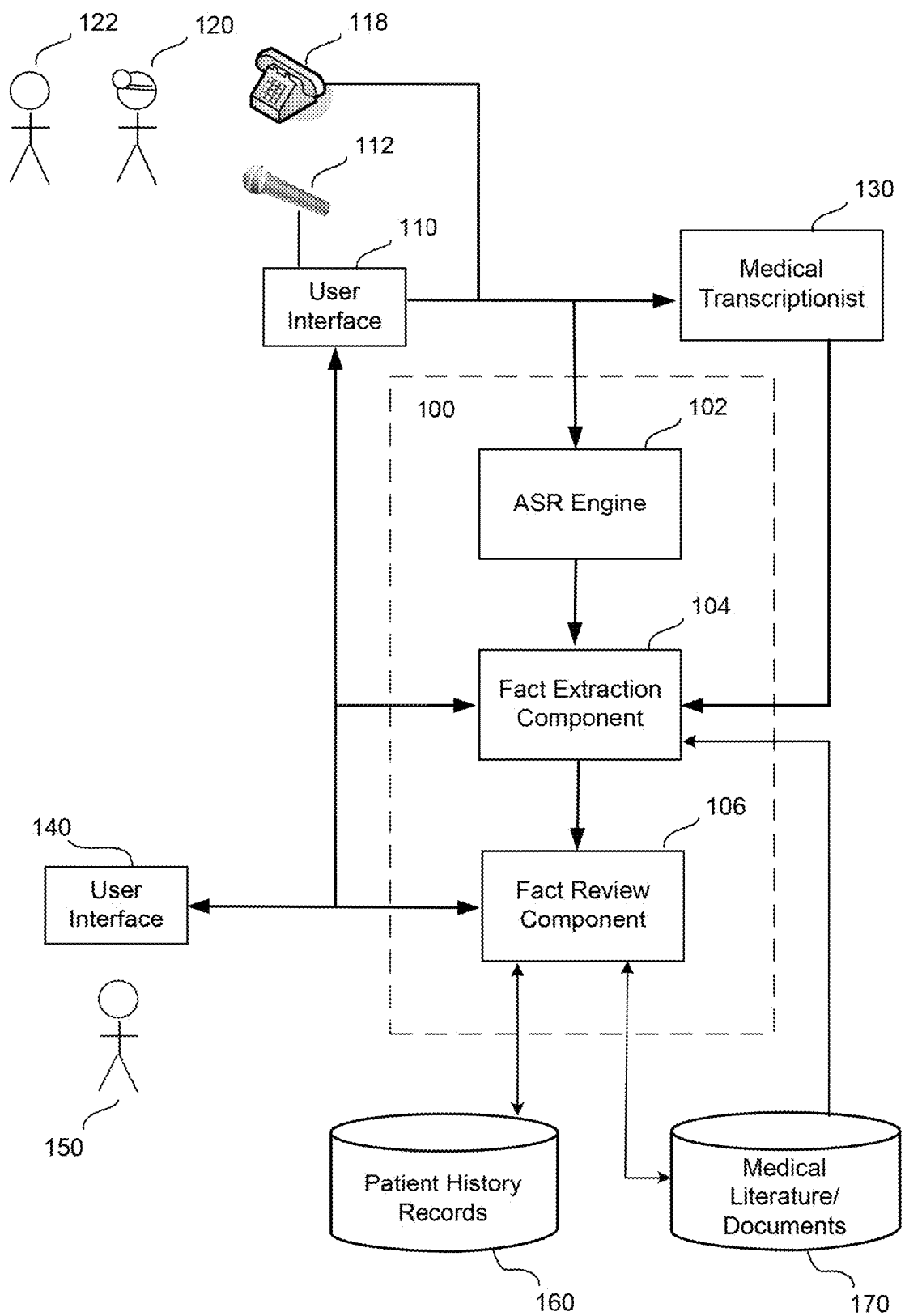
FIG. 1 is a block diagram of an exemplary operating environment for a clinical language understanding (CLU) system that may be employed in connection with some embodiments.

The inventors have recognized that the initial documentation provided by clinicians for patient encounters is often insufficient for medical coders to code accurately, leading in some cases to decreased revenue, fraud risk, and the potential for substantial recoveries for coding errors. As described elsewhere herein, clarification requests may be made to clinicians by Clinical Documentation Specialists (CDSes) via operation of a Clinical Documentation Improvement (CDI) system, to improve the documentation. The inventors have appreciated that notifying medical coders of the existence of CDI clarification requests at the time the requests are being addressed may provide the benefit of improving coding accuracy by alerting the coder to additional forthcoming information regarding the patient encounter. For example, a coder having knowledge of a pending CDI clarification request may be alerted to await additional documentation to avoid over- or under-billing for the patient encounter.

Accordingly, in some embodiments, a medical coding system may be configured to receive notifications of CDI clarification requests from a CDI system. In some embodiments, a medical coding system may be configured to present the coder with documents that represent CDI clarification requests created by CDSes or a CLU system for the same patient encounter.

In some embodiments, the CDI clarification requests may be made available to coders while the encounter is being currently coded. This information may be made visible to coders as documents, as soon as it is available. Some embodiments may also present coders with details about documentation discrepancies, clarifications, corrections, and other communications that may have transpired during the CDI process. These clarifications may show up as documents within the coder's user interface.

In some embodiments, the use of clarifications in the coding interface may also eliminate redundant or duplicate queries that the coder may otherwise have made, eliminating the resultant delay from waiting for a response, as well as the undesirable time, expense, and inconvenience for a clinician to answer redundant or duplicate queries, in some embodiments.

In some embodiments, increased accuracy and specificity of codes may be achieved based on awareness of the clarification requests, thereby improving billing efficiency. By thereby facilitating clinicians to create more complete and compliant clinical documentation, a medical coding system as described may also improve coding, downstream revenue cycle processes, and quality reporting processes, in some embodiments.

While a number of inventive features for clinical documentation processes are described above, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciate that these examples are provided merely for purposes of illustration, and that other implementations are possible.

Clinical Language Understanding (CLU) System

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack", "acute myocardial infarction", "acute MI" and "AMI". To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410", where 410 is the code number for "acute myocardial infarction" according to the ninth edition of the ICD standard.

To allow clinicians and other healthcare, personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

While some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present invention are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques, such as a natural language understanding (NLU) engine. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. 495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

Some embodiments described herein may make use of a clinical language understanding (CLU) system, an exemplary operating environment for which is illustrated in FIG. 1. CLU system 100, illustrated in FIG. 1, may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104 and fact review component 106 may be implemented as a separate component of system 100, or any combination of these components may be integrated into a single component or a set of distributed components. In addition, any one of ASR engine 102, fact extraction component 104 and fact review component 106 may be implemented as a set of multiple software and/or hardware components. It should be understood that any such component depicted in FIG. 1 is not limited to any particular software and/or hardware implementation and/or configuration. Also, not all components of exemplary system 100 illustrated in FIG. 1 are required in all embodiments. For example, in some embodiments, a CLU system may include functionality of fact extraction component 104, which may be implemented using a natural language understanding (NLU) engine, without including ASR engine 10:2 and/or fact review component 106.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments, medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semiautomatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120.

However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present invention are not limited in this respect. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method." U.S. Pat. No. 7,493,253 is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack", "acute MI" and "AMI" may all be linked to the same abstract concept in the formal ontology a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction".

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack". Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation", "brain" and "meningitis" may allow the fact extraction component to automatically extract a fact corresponding to "meningitis", despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present invention are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the invention are not limited in this respect. In addition, a knowledge representation model such as an ontology used by fact extraction component 104 may be constructed in any suitable way, as aspects of the invention are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." in some embodiments, automatically generated and hard coded (e.g., by a human developer) concepts and/or relationships may both be included in a knowledge representation model used by fact extraction component 104.

As discussed above, it should be appreciated that aspects of the invention are not limited to any particular technique(s) for constructing knowledge representation models. Examples of suitable techniques include those disclosed in the following:

Gómez-Perez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and C. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL '04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as -ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$, of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 ... fn having respective probabilities p1 ... pn of being associated with a "Problem" entity label, the statistical model may be trained to apply respective weights w1 ... wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in die sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute"

relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

Figure 2:
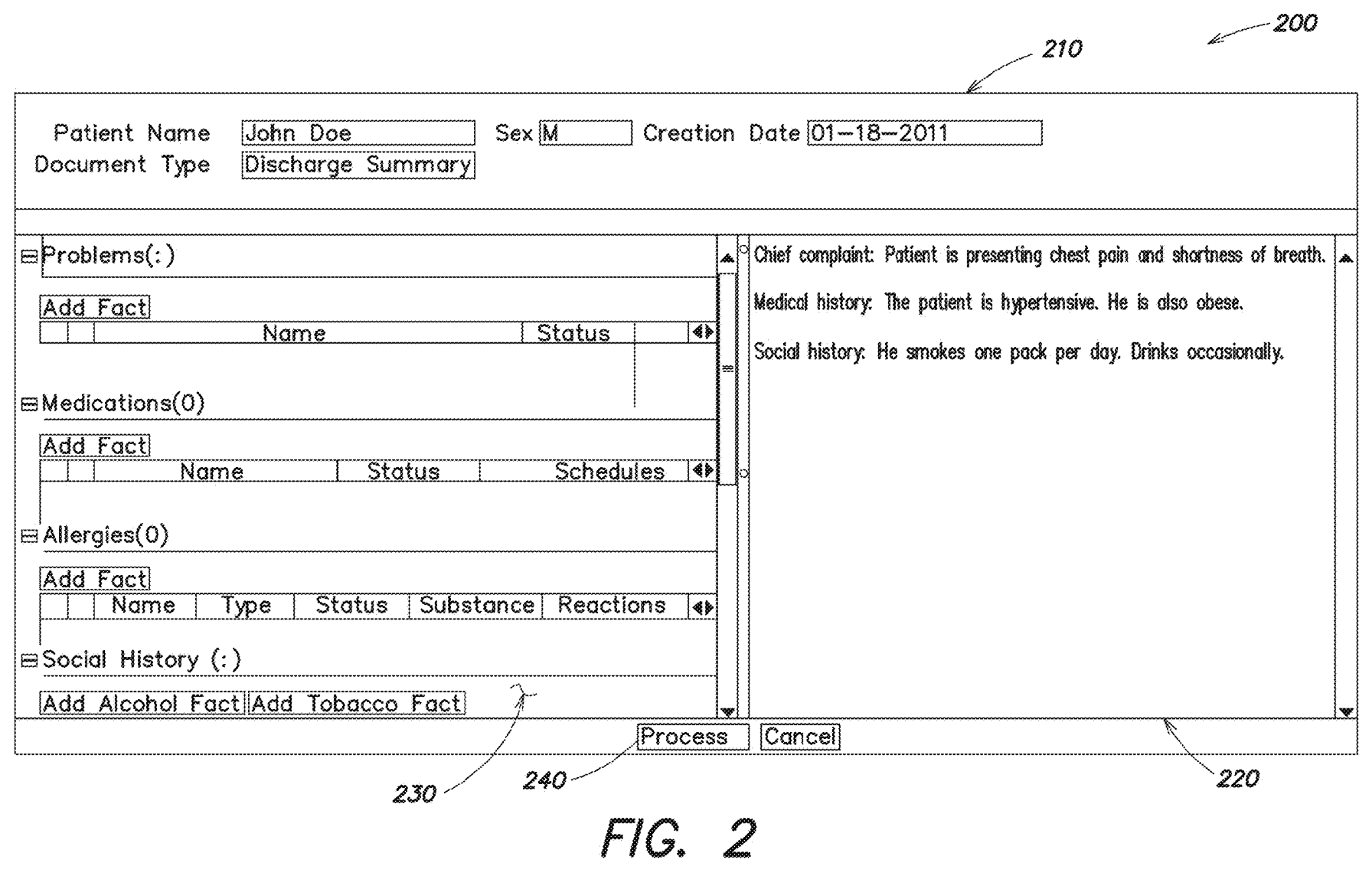

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3A:
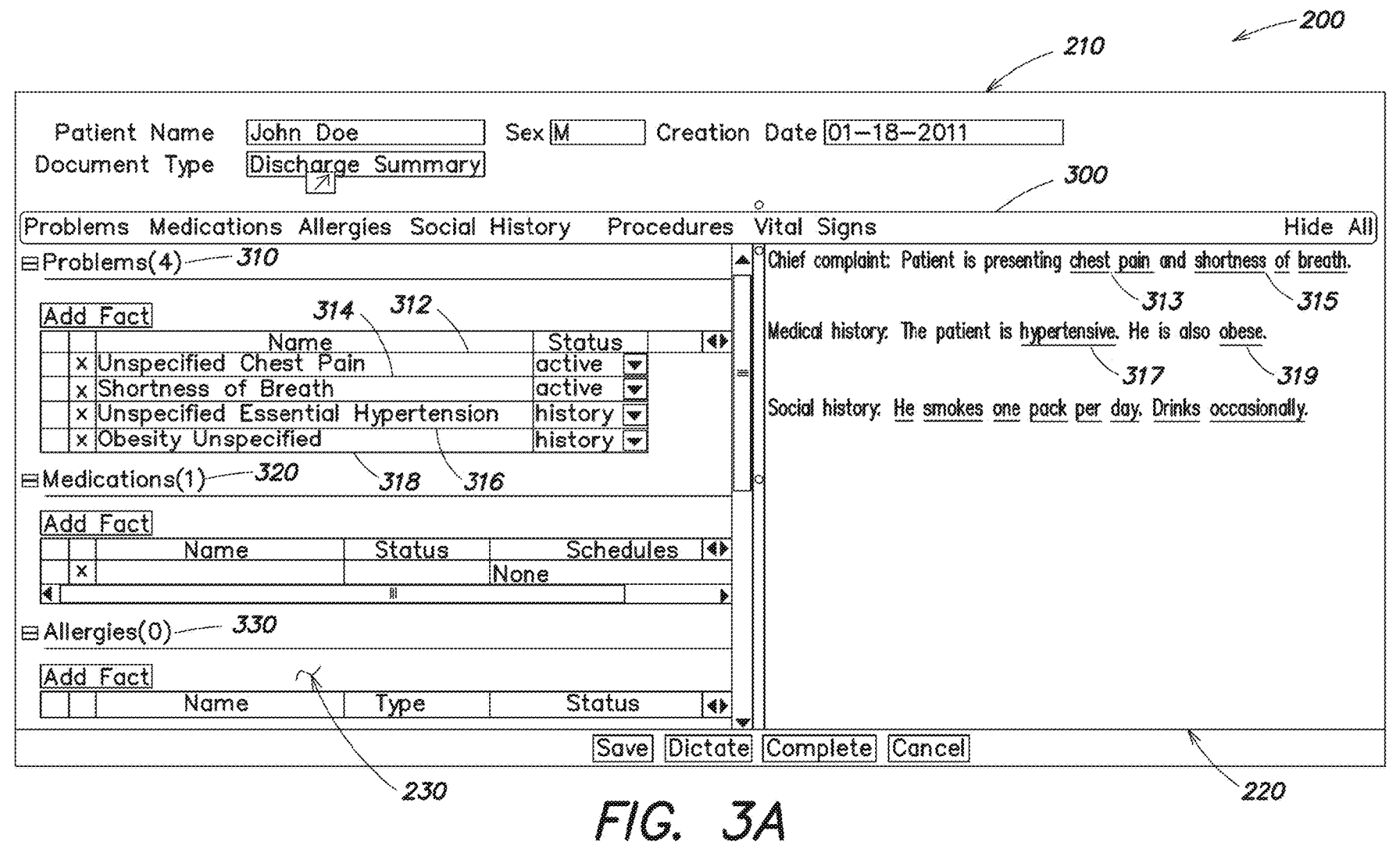
Figure 3B:
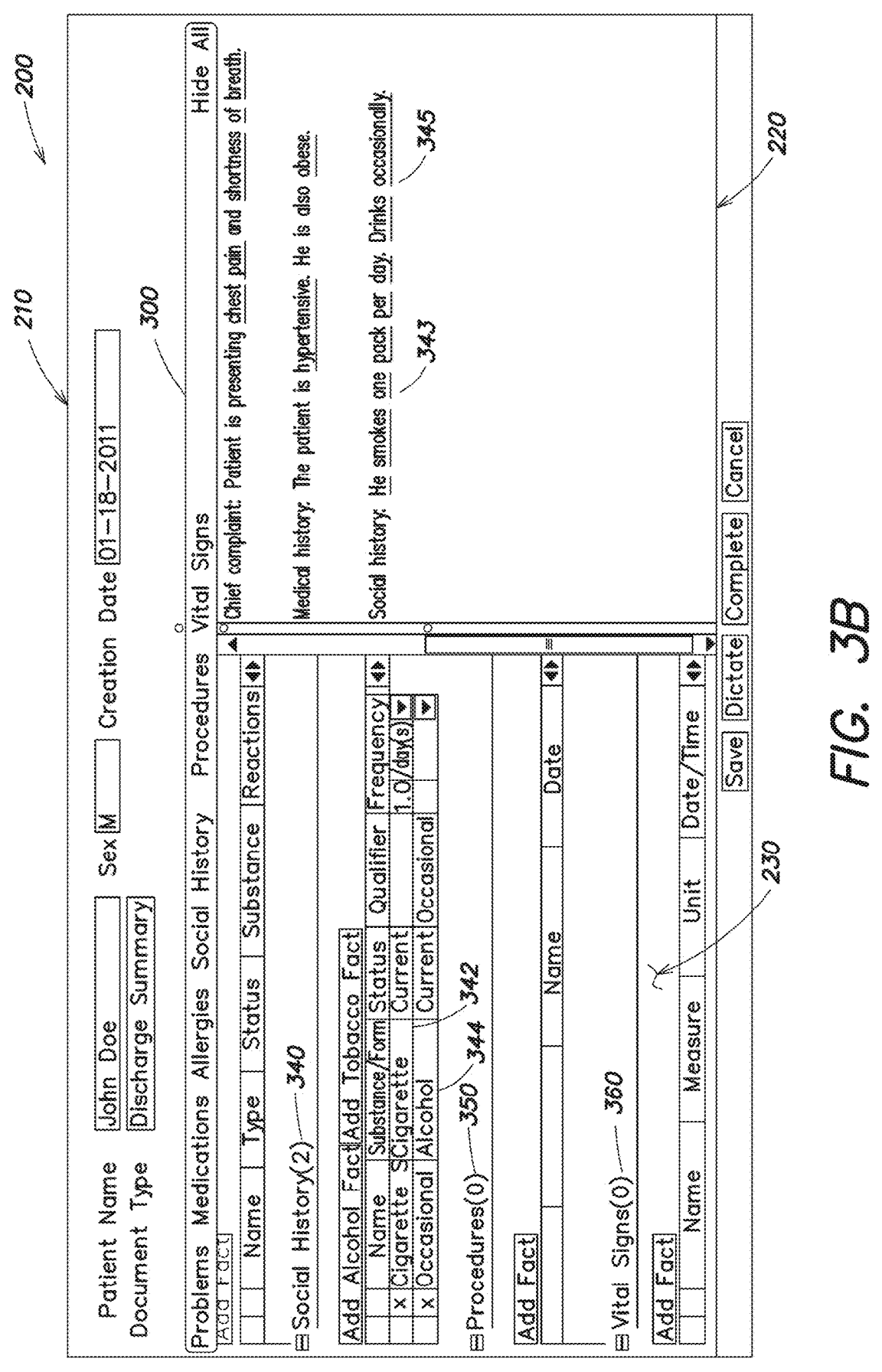

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active". Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine. (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary list of fact categories and component fields:
Category: Problems. Fields: Name, SNOMED status, ICD code.
Category: Medications. Fields: Name, Status, Dose form, Frequency. Measures, RxNorm code, Administration condition, Application duration, Dose route.
Category: Allergies. Fields: Allergen name, Type, Status, SNOMED code, Allergic reaction, Allergen RxNorm.
Category: Social history Tobacco use. Fields: Name, Substance, Form, Status, Qualifier, Frequency, Duration, Quantity, Unit type, Duration measure, Occurrence, SNOMED code, Norm value, Value.
Category: Social history—Alcohol use. Fields: Name, Substance, Form, Status, Qualifier, Frequency, Duration, Quantity, Quantifier, Unit type, Duration measure, Occurrence, SNOMED code, Norm value, Value.
Category: Procedures. Fields: Name, Date, SNOMED code.
Category: Vital signs. Fields: Name, Measure, Unit, Unit type. Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 31:2 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint". In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain". In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to provide any of various ways for the user to make one or more changes to the set of medical facts extracted from the text narrative by fact extraction component 104 and displayed in fact panel 230, and these changes may be collected by fact review component 106 and applied to the documentation of the patient encounter. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
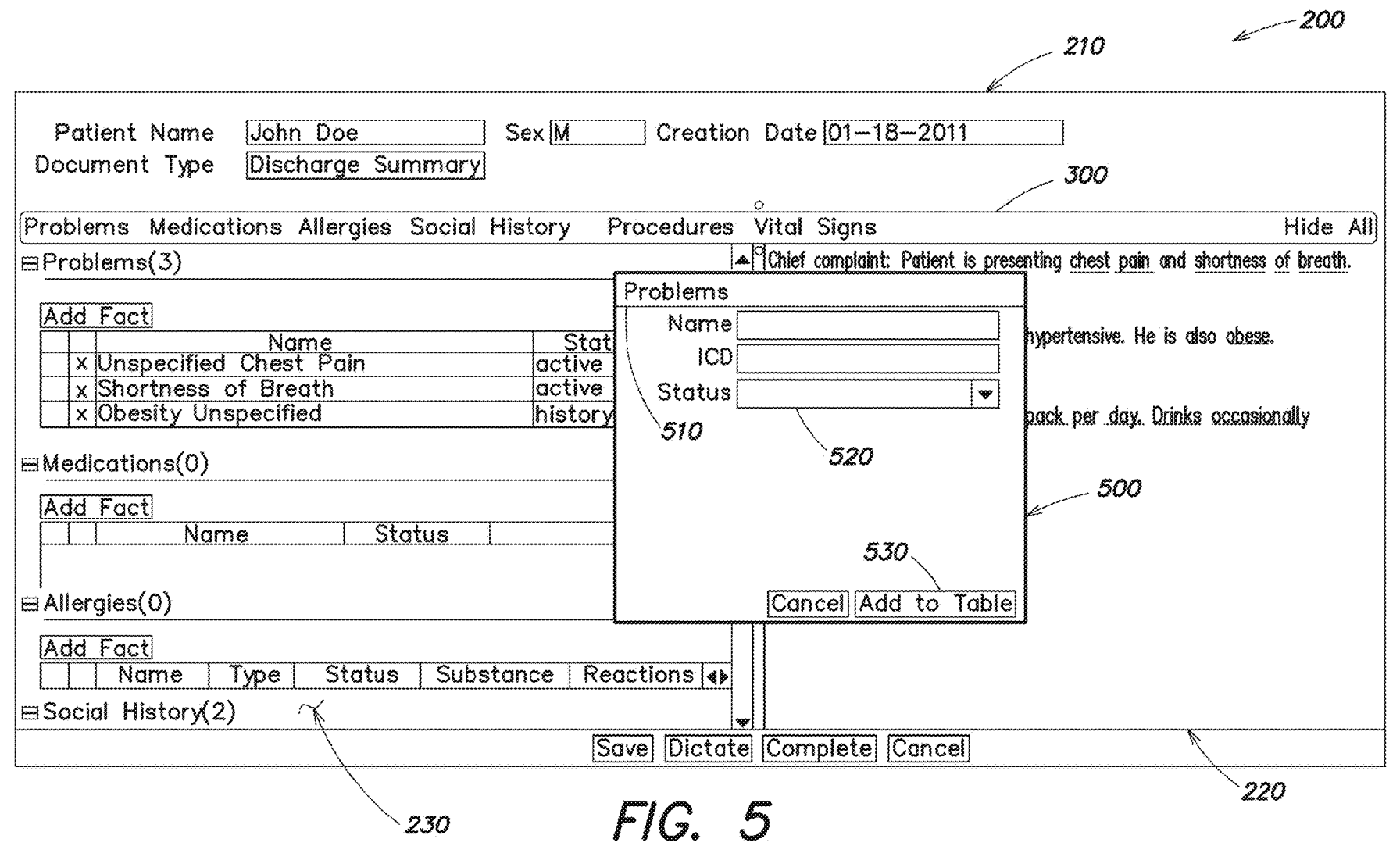

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item. In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

Figure 6:
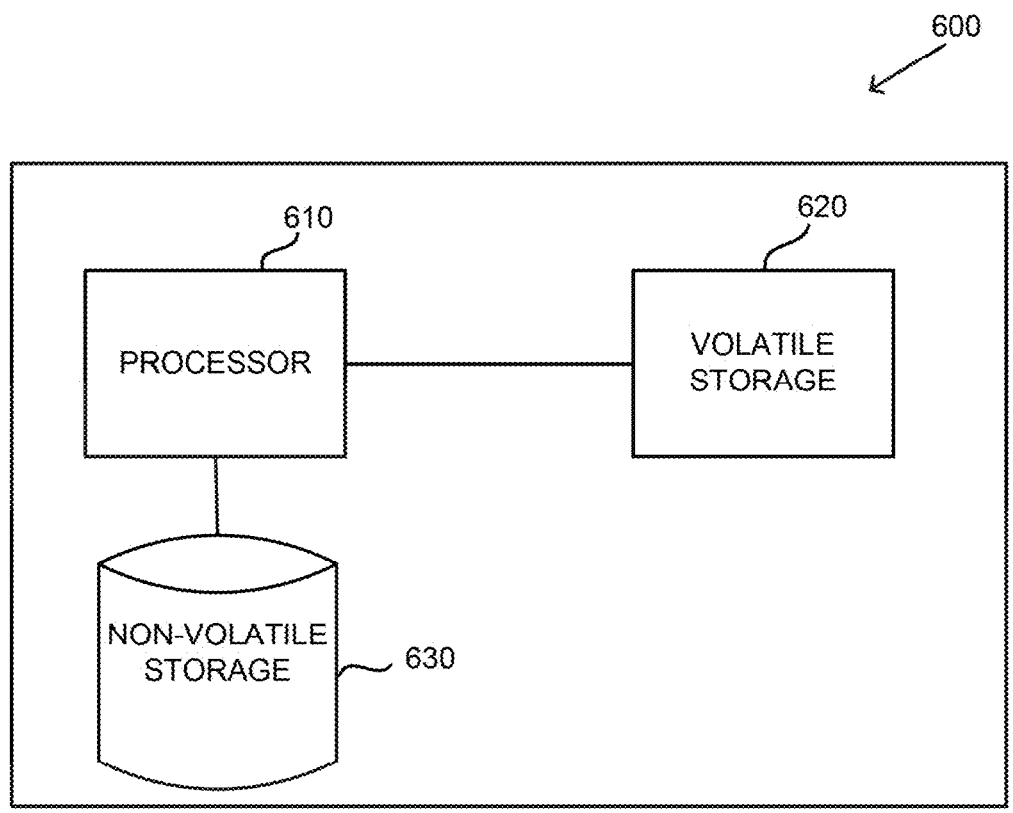
FIG. 6 is a block diagram of an exemplary computer system on which aspects of some embodiments may be implemented.

A CLU system in accordance with the techniques described herein may take any, suitable form, as aspects of the present invention are not limited in this respect. An illustrative implementation of a computer system 600 that may be used in connection with some embodiments of the present invention is shown in FIG. 6. One or more computer systems such as computer system 600 may be used to implement any of the functionality described above. The computer system 600 may include one or more processors 610 and one or more tangible, non-transitory computer-readable storage media (e.g., volatile storage 620 and one or more non-volatile storage media 630, which may be formed of any suitable non-volatile data storage media). The processor 610 may control writing data to and reading data from the volatile storage 620 and the non-volatile storage device 630 in any suitable manner, as the aspects of the present invention are not limited in this respect. To perform any of the functionality described herein, the processor 610 may execute one or more instructions stored in one or more computer-readable storage media (e.g., volatile storage 620), which may serve as tangible, non-transitory computer-readable storage media storing instructions for execution by the processor 610.

Computer-Assisted Coding (CAC) System

As discussed above, medical coding has conventionally been a manual process whereby a human professional (the "coder") reads all of the documentation for a patient encounter and enters the appropriate standardized codes (e.g., ICD codes, HCPCS codes, etc.) corresponding to the patient's diagnoses, procedures, etc. The coder is often required to understand and interpret the language of the clinical documents in order to identify the relevant diagnoses, etc., and assign them their corresponding codes, as the language used in clinical documentation often varies widely from the standardized descriptions of the applicable codes. For example, the coder might review a hospital report saying, "The patient coded at 5:23 pm." The coder must then apply the knowledge that "The patient coded" is hospital slang for a diagnosis of "cardiac arrest," which corresponds to ICD-9-CM code 427.5. This diagnosis could not have been identified from a simple word search for the term "cardiac arrest," since that standard term was not actually used in the documentation; more complex interpretation is required in this example.

As also discussed above, conventional medical coding systems may provide a platform on which the human coder can read the relevant documents for a patient encounter, and an interface via which the human coder can manually input the appropriate codes to assign to the patient encounter. By contrast, some embodiments described herein may make use of a type of medical coding system referred to herein as a "computer-assisted coding" (CAC) system, which may automatically analyze medical documentation for a patient encounter to interpret the document text and derive standardized codes hypothesized to be applicable to the patient encounter. The automatically derived codes may then be suggested to the human coder, clinician, or other user of the CAC system. In some embodiments, the CAC system may make use of an NLU engine to analyze the documentation and derive suggested codes, such as through use of one or more components of a CLU system such as exemplary system 100 described above. In some embodiments, the NLU engine may be configured to derive standardized codes as a type of medical fact extracted from one or more documents for the patient encounter, and/or the CLU system may be configured to access coding rules corresponding to the standardized code set(s) and apply the coding rules to extracted medical facts to derive the corresponding codes.

In some embodiments, the CAC system may be configured to provide a user interface via which the automatically suggested codes may be reviewed by a user such as a medical coder. The user interface may take on any of numerous forms, and aspects of the invention are not limited to any particular implementation. Like the user interfaces for the CLU system 100 described above, the user interface for the CAC system may provide tools that allow a coder to interact with the CAC system in any suitable form, including visual forms, audio forms, combined forms, or any other form providing the functionality described herein. When the tools are provided in visual form, their functionality may be accessed in some embodiments through a graphical user interface (GUI), which may be implemented in any suitable way. An example of a suitable GUI 700 for a CAC system is illustrated in FIG. 7A.

The exemplary GUI 700 provides the user with the ability to simultaneously view the list of codes for a patient encounter along with the documentation from which the codes are derived. Some embodiments may also allow the user to view structured encounter- or patient-level data such as the patient's age, gender, etc. (not shown in FIG. 7A), some or all of which information may be useful in arriving at the appropriate codes for the patient encounter. In panel 710 is displayed a list of available documents for the patient encounter currently being coded. In the example illustrated in FIG. 7A, these include two History & Physical reports, a Discharge Summary, an Emergency Room Record, a Consultation report, a Progress Note, and an Operative Report.

Indicator 712 shows that the current document being viewed is the Discharge Summary dated Jun. 18, 2014, and this document appears in panel 720 where the user can view the text of the document. Shown in panel 730 is the current list of codes for the patient encounter. An indicator 732 shows, for each code in the list, whether the code was automatically suggested or added manually by the user. In this particular example, the empty circles indicate that all of the codes in the current list were automatically suggested by the CAC system.

Exemplary GUI 700 also provides the user with the ability to view and/or query which portion(s) of the available documentation gave rise to the suggestion of which code(s) in the list of codes for the patient encounter. In some embodiments, any suitable indicator(s) may be provided of the link between a particular code and the portion(s) of the documentation text from which the code was derived. Each automatically suggested code may be linked to one or more portions of text from which the code was derived, and each linked portion of text may be linked to one or more codes that are derivable from that portion of text. For instance, viewing together FIGS. 7A and 7D, which show the Discharge Summary viewed at different scroll locations in panel 720, it can be seen that there are two different mentions of "respiratory failure" in the document from which code 518.81 may have been derived (an example of a link between a code and multiple portions of text), and that there are two different codes 303.90 and 571.5 that may have been derived at least in part from the mention of "Alcoholism" in the text (an example of a link between a portion of text and multiple codes).

Figure 7B:
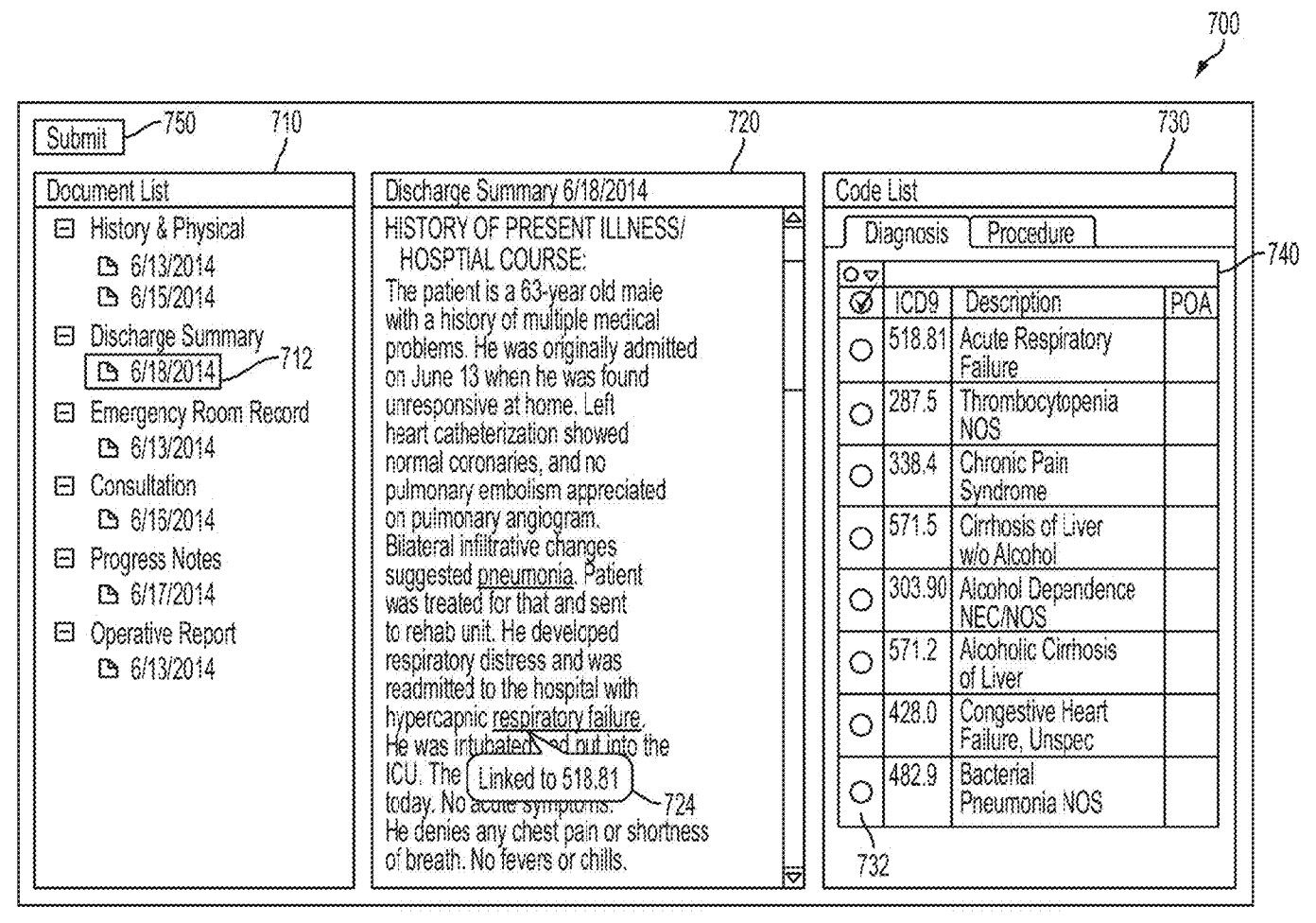

In the example of FIG. 7A, an indicator 722 is provided (underlining in this particular example) to visually distinguish portions of the document text linked to codes in the current list. Exemplary GUI 700 also allows the user to query a particular linked portion of text to see which code(s) are linked to that portion of text. FIG. 7B illustrates an exemplary indicator 724 of the corresponding link that may be displayed in response to the user querying the linked portion of text in any suitable way, such as by selecting or hovering over it with the mouse pointer. Exemplary GUI 700 further allows the user to query a particular code to see which portion(s) of text are linked to that code. FIG. 7C illustrates exemplary way of querying code 287.5 by right-clicking on the listed code in panel 730 and selecting "Show Highlights" in the context menu that then appears. In response, the document in which the linked text appears is displayed in panel 720 (in this case it is the same Discharge Summary, scrolled to a particular section), and the linked text is visually distinguished by indicator 726 (highlighting in this particular example), as illustrated in FIG. 7D.

If the user disagrees with the linked text and does not believe that the suggested portion(s) of text actually should correspond with the linked code, the user can select "Unlink Text" in the context menu of FIG. 7C to cause the link between that code and the corresponding text to be discarded. The user can also manually create a new link between a code and one or more portions of text, e.g., by selecting "Link Text" in the context menu of FIG. 7C and highlighting or otherwise designating the portion(s) of text in the documentation which should be linked to the selected code.

Exemplary GUI 700 further allows the user to accept or reject each of the automatically suggested codes, e.g., using the context menu of FIG. 7C for each suggested code. FIG. 7E illustrates exemplary indicators 734 and 736 which replace indicator 732 for each code that has been accepted or rejected, respectively. In this example, the user has accepted most of the suggested codes, but has rejected code 571.5 because the user believes the mention of "Alcoholism" in the documentation makes the diagnosis of "Cirrhosis of Liver w/o Alcohol" incorrect. Exemplary GUI 700 further allows the user to provide a reason for the rejection of a code, such as by using the exemplary context menu illustrated in FIG. 7F, In some embodiments, the reasons provided by users for rejecting particular automatically suggested codes may be used for review and/or training purposes (e.g., for training the NLU engine, e.g., of the CLU system to derive more accurate codes from documentation text).

GUI 700 may also allow the user to replace a code with a different code, instead of rejecting the code outright, e.g., using the context menu of FIG. 7C. In the example illustrated in FIG. 7E, the user has replaced code 482.9 with code 482.1, and indicator 738 shows that the new code was user-added. 482.9 (Pneumonia due to *Pseudomonas*) is a more specific diagnosis applicable to the patient encounter than the suggested 482.1 (Bacterial Pneumonia, Unspecified), so the user may provide "More specific code needed" as the reason for the replacement. In some embodiments, when a user replaces an automatically suggested code with a different code, any documentation text that was linked to the originally suggested code may then be linked to the replacement code. Such replacement codes, optionally with linked text and/or replacement reasons, may also be used as feedback, e.g., for training of the CLU system.

The user can also add a code to the list for a patient encounter by manually inputting the code in input field 740. For example, FIG. 7E shows a new code 041.7 that has been added by the user. The user may link the added code to supporting portion(s) of the text, such as the mention of "*pseudomonas*" in the Discharge Summary, e.g., by using the "Link Text" procedure described above.

When the user has completed the review of the codes and supporting documentation, exemplary GUI 700 allows the user to submit the codes for finalization by selecting button 750. FIG. 8 illustrates an exemplary code finalization screen 800 that may be displayed following the user's selection of submit button 750. In exemplary screen 800, all of the accepted and user-added codes are displayed for final review. Alternatively, in some embodiments the user may be required to affirmatively accept even user-added codes before they will appear in code finalization screen 800. The codes are displayed in screen 800 in an ordered sequence, which the user may change by re-ordering the codes. In some embodiments, the order of the finalized sequence of codes may be used in later processes such as billing, to determine the principal diagnosis, etc. Exemplary screen 800 also includes fields for "present on admission" (POA) indicators, which provide information on whether each diagnosis was present when the patient was admitted to the hospital, or was acquired during the hospital stay. This information may be required documentation in some circumstances, and in some embodiments may be used for review and/or training purposes. In some embodiments, POA indicators may be automatically suggested, e.g., using the CLU system; while in other embodiments, POA indicators may only be input manually.

When the user is satisfied with the finalized sequence of codes, exemplary screen 800 provides a button 810 for the codes to be saved, at which the coding process for the patient encounter becomes complete. In some embodiments, the CAC system may compare the finalized sequence of codes with stored coding rules, and may present the user with any applicable error or warning notifications prior to saving. As discussed above, once saved, the finalized sequence of codes may be sent to other processes such as billing and quality review, and in some embodiments may be used for performance review and/or training of the CLU and/or CAC systems.

Figure 9:
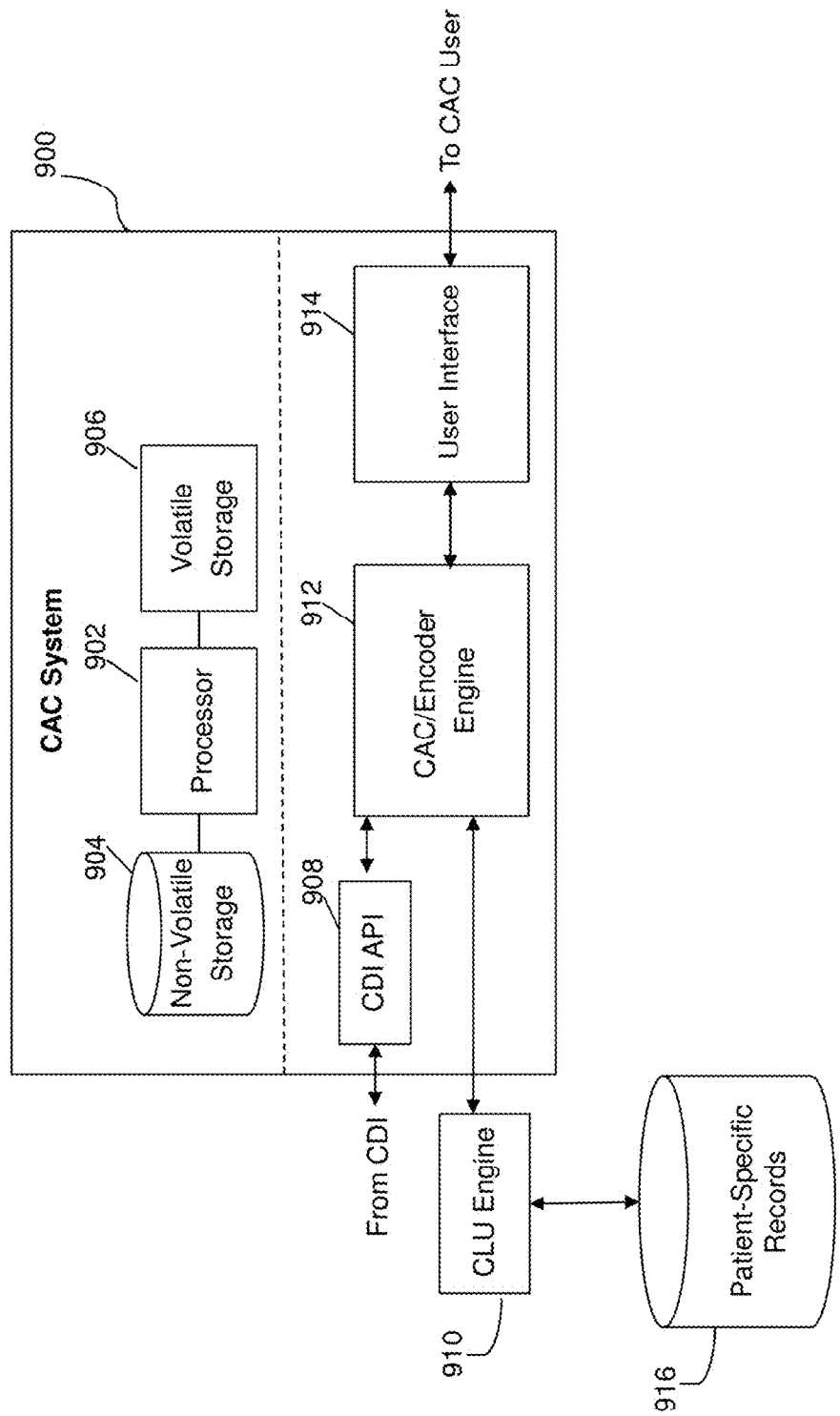
FIG. 9 is a block diagram of an exemplary computer-assisted coding (CAC) system in accordance with some embodiments.

FIG. 9 is a schematic block diagram of an exemplary CAC system, in accordance with some embodiments. As shown, the architecture 900 may include a processor 902, non-volatile storage 904, and volatile storage 906, as described further below. CAC system 900 may also include a CAC/encoder engine 912, user interface 914, and CDI API 908. CAC system 900 may be in communication with CLU system 910, which may store and retrieve patient-specific record information to and from database 916.

In some embodiments, CAC/encoder engine 912 may perform operations including associating entered codes with patient records and suggesting codes for association with patient records. Suggested codes may be derived from or received from a CLU system 910, in some embodiments. Suggested codes may be presented to a CAC user, e.g., a coder, for approval via user interface 914. Codes may also be received from the CAC user via user interface 914. In some embodiments, user interface 914 may be used to display documents relating to a patient's health records to the CAC user. In some embodiments, as discussed below, these displayed documents may include one or more clarification requests, which may be received from a CDI system via CDI API 908.

In some embodiments, CDI API 908 may be used to request clarification requests from a CDI system, such as CDI system 1100 described below. CDI API 908 may communicate with a CAC API on the CDI system to request any and/or all clarification requests on a system, or clarification requests associated with a specific patient, or clarification requests associated with a particular code or codes associated with the specific patient. CDI API 908 may use one or more networks, including packet-based and/or IP networks such as the Internet or private intranets, to communicate with a CDI system and to receive information and/or documents pertaining to clarification requests. In some embodiments, communications with the CDI system may be encrypted, to prevent access by parties not authorized to view the specific patient information and to provide compliance with health record privacy regulations such as HIPAA (in the U.S., the Health Insurance Portability and Accountability Act of 1996).

Like the embodiments of the CLU system 100 described above, the CAC system 900 in accordance with the techniques described herein may take any suitable form, as aspects of the present invention are not limited in this respect. One or more computer systems may be used to implement any of the functionality of the CAC system 900 described above. As shown, CAC system 900 may include one or more processors 902 and one or more tangible, non-transitory computer-readable storage media (e.g., volatile storage 906 and one or more non-volatile storage media 904, which may be formed of any suitable non-volatile data storage media). The processor 902 may control writing data to and reading data from the volatile storage 906 and the non-volatile storage media 904 in any suitable manner, as aspects of the present invention are not limited in this respect. To perform any of the functionality described herein, the processor 902 may execute one or more instructions stored in one or more computer-readable storage media (e.g., volatile storage 906), which may serve as tangible, non-transitory computer-readable storage media storing instructions for execution by the processor 902.

Clinical Documentation Improvement (CDI) System

As briefly noted above, a CDI system, such as the CDMP Guide product offered by JATA, provides a tool for a user to examine patient specific records for compliance with standard formats and protocols, to issue clarification requests to clinicians or others for clarification or supplementation of factual data, and to otherwise ensure that medical records are as complete and accurate as possible. Such accuracy and completeness may be important, for example, to ensure that appropriate codes may be assigned for billing and record keeping purposes, such as Diagnosis Related Group (DRG) codes or ICD-9-CM Diagnosis Codes used for Medicare or other billing purposes.

Figure 10:
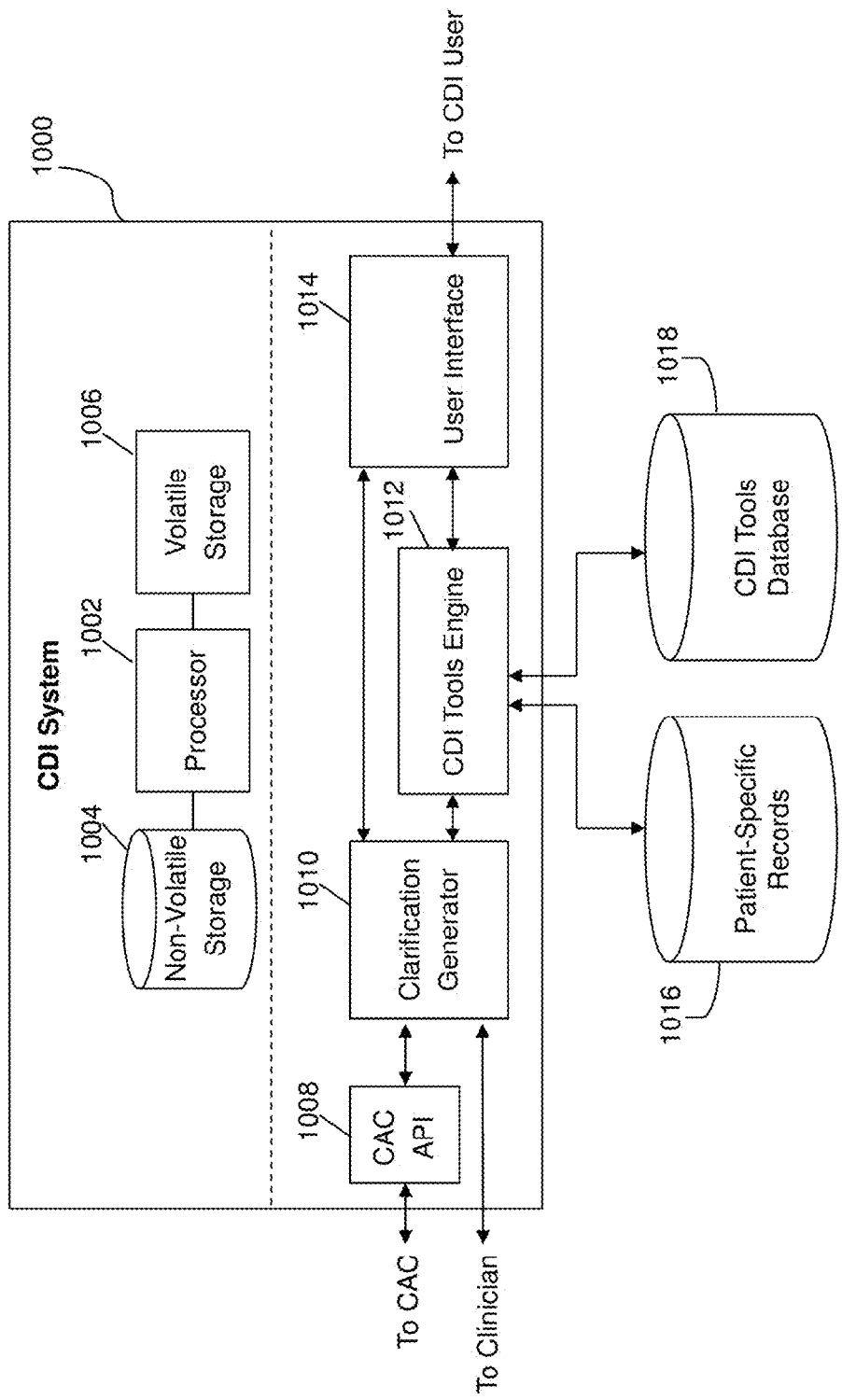
FIG. 10 is a block diagram of an exemplary clinical document improvement (CDI) system in accordance with some embodiments.

An example of a CDI system architecture 1000 that may be employed in various embodiments of the invention is shown in FIG. 10. As shown, the architecture 1000 may include a processor 1002, non-volatile storage 1004, and volatile storage 1006, as described further below. CDI system 1000 may also include a CDI tools engine 1012, a user interface 1014, a database 1016 for storing patient specific records, and a database 1018 for storing documentation and data the CDI tools engine 1012 may use to implement the CDI process. In other embodiments, only a single database or other storage mechanism, or one or more databases in addition to those illustrated, may alternatively be used both for storing patient specific records and for providing resources for the CDI process.

The database 1018 may, for example, contain data reflecting nested menus of diagnosis possibilities corresponding to DRG, ICD-9-CM or other codes, as well as corresponding descriptive material, that allow a CDS to drill down to a specific diagnosis that can be used for billing and record keeping purposes. Should more detail be required in order to pinpoint a particular diagnosis, to clarify an ambiguity, or to fill in gaps in a record of a patient encounter, the CDS can use the CDI tools engine 1012 and clarification generator 1010 to generate a request for clarification or additional detail from the clinician.

The user interface 1014 may take on any of numerous forms, and the invention is not limited to any particular implementation. Like the user interfaces for the CLU system 100 described above, the user interface 1014 may provide tools that allow a CDS to interact with the CDI system 1000 in any suitable form, including visual forms, audio forms, combined forms, or any other form providing the functionality described herein, as embodiments are not limited in this respect. When the tools are provided in visual form, their functionality may be accessed through a graphical user interface (GUI).

Like the embodiments of the CLU system 100 described above, the CDI system 1000 in accordance with the techniques described herein may take any suitable form, as aspects of the present invention are not limited in this respect. One or more computer systems may be used to implement any of the functionality of the CDI system 1000 described herein. As shown, CDI system 1000 may include one or more processors 1002 and one or more tangible, non-transitory computer-readable storage media (e.g., volatile storage 1006 and one or more non-volatile storage media 1004, which may be formed of any suitable non-volatile data storage media). The processor 1002 may control writing data to and reading data from the volatile storage 1006 and the non-volatile storage media 1004 in any suitable manner, as embodiments are not limited in this respect. To perform any of the functionality described herein, the processor 1002 may execute one or more instructions stored in one or more computer-readable storage media (e.g., volatile storage 1006), which may serve as tangible, non-transitory computer-readable storage media storing instructions for execution by the processor 1002.

In some embodiments, CDI system 1000 may be in communication with a medical coding system such as a computer-assisted coding system via CAC API 1008. CAC API 1008 may receive clarification information from clarification generator 1010. Clarification generator 1010 may be in communication with user interface 1014, which may be used to display information to, and to receive instructions from, a user such as a CDS. CDI tools engine 1012 may be in communication with both clarification generator 1010 and user interface 1014. As well, in some embodiments, CDI tools engine 1012 may be in communication with databases 1016 and 1018. Database 1016 may be a database of patient-specific records, and in some embodiments may be the same database as database 916 described above. Database 1018 may be a database storing documentation and data the CDI tools engine 1012 may use to implement the CDI process.

Clarification Request Handling
Process and Workflow

In some embodiments, a clarification request for resolution by a clinician may be generated with a CDI system, and notification of the clarification request may be transmitted to a medical coding system. In some embodiments, die medical coding system may be a manual coding system, while in other embodiments, the medical coding system may be a system configured to automatically suggest medical codes, such as the exemplary CAC system described above. The clinician may resolve the clarification request, e.g., by providing the information requested in the clarification request, such as in a direct response to the clarification request or in an addendum to a document previously created by the clinician.

In some embodiments, both the clarification request and the response thereto may be sent to the medical coding system. In some embodiments, a response of the clinician to the clarification request may be received at the CDI system, and forwarded to the medical coding system. In some embodiments, a copy of the response may be received directly at the medical coding system from the clinician. In some embodiments, the response may be a document, such as a letter, a report, a note, a diagnostic test result, an image or imaging test result, or other document. In some cases, the clinician's response document may be an addendum to a previous document created for the patient encounter, or a revised version of a previous document, providing clarification regarding the issue identified in the clarification request. In some embodiments, the response may be sent via an electronic health record (EHR) system; in other embodiments, the response may be collected as a miscellaneous external document.

In some embodiments, a notification of a clarification request generated at a CDI system for resolution by a clinician may be received at a medical coding system. In some embodiments, the medical coding system may be a CAC system. Examples of possible functionality of such a CAC system are described above. The notification may indicate an event such as the generation of the clarification request, the transmission of the clarification request to the clinician, the review of the clarification request by the clinician, or another event relating to the clarification request. In some embodiments, the notification may be sent and/or received at substantially the same time as the occurrence of the identified event. In some embodiments, a notification of the clarification request may be presented to a user at the medical coding system in association with at least one medical document for which the clarification request was generated at the CDI system. In some embodiments, the notification may be presented to a user via a user interface of the medical coding system, such as exemplary GUI 700 described above. For example, in some embodiments, when a clarification request relates specifically to a particular document in document list 710, a suitable indicator of the clarification request may be displayed in association with the particular document in panel 710, and/or upon viewing of the particular document in panel 720. In some embodiments, as discussed further below, the clarification request may be presented to the user of the medical coding system as a peer document with medical records for the patient encounter.

In some embodiments, coders may be able to obtain, via a user interface, information about a clarification document. The information may include one or more of: information about the source of the document; the Diagnosis Related Group (DRG) code(s) or other codes identified by a CDS; a physician associated with the document; details about the discrepancy leading to the CDI clarification request; resolution information regarding the clarification, if available; or other information. The appearance of a clarification request notification may reflect, in some embodiments, the fact that a clarification request was generated and sent to a clinician. In some embodiments, further information regarding the transmission of the clarification request, such as the time and date of the clarification request, may be sent to the medical coding system.

In some embodiments, if a clarification request is received during the coding process, a coding system user may be alerted in real time of the arrival of the clarification request, or a response to the clarification request. The coding system user may then, in some embodiments, be enabled to review the entirety of a clarification request, or a summary version. By doing so, improvements in coding quality may result, in some embodiments. For example, in some embodiments, informing the coder that a clarification request is pending may alert the coder to wait for additional information before finalizing the codes for the patient encounter, thereby improving the accuracy of the eventually submitted codes. In some embodiments, notes may be passed between CDSes and coders. The transfer of preliminary or initial codes may also be performed.

In some embodiments, the coding system user may be enabled to associate a tag or note with the finalized sequence of codes, indicating that more information is expected, if a CDI clarification request appears on the system but a response from a clinician does not appear. The tag or note may subsequently be displayed. In some embodiments, the CDI system, in addition to the medical coding system, may be configured to allow the CDS to also enter medical billing codes for the patient encounter. In some such embodiments, the codes entered by the CDS may be included with the CDI clarification request, and/or sent from the CDI system to the medical coding system. In some cases, a clarification request may be associated with a particular code, which may alert the coder to the fact that there is a question related to that particular code that may require changing that code before finalizing the encounter. In some such embodiments, an indicator of an associated clarification request may be provided in response to user selection of the particular code in the coding interface. The codes being viewed by the CDS at the time a clarification request was generated may be sent to the medical coding system in some embodiments as well. When the CDI system sends codes to a medical coding system, in some embodiments the coder can get a head start on the coding process using these codes. In some embodiments, when codes are sent from the CDI system to the medical coding system, the coder may view the codes in a user interface. The coder may also approve the codes, thereby enabling the coder to accelerate his or her work in coding the encounter.

In some embodiments, the medical coding system, in addition to the CDT system, may be configured to allow the coder to also generate clarification requests. In some such embodiments, generation and/or transmission of a duplicate clarification request matching a clarification request already generated at the CDI system may be suppressed at the medical coding system. A duplicate clarification request may be a clarification request for substantially the same information requested in a prior clarification request, or for information addressing substantially the same issue noted by the CDS in the current documentation of the patient encounter, etc.

In some embodiments, the clinician's response to a clarification request, and/or the clarification request itself, may be analyzed at the CAC system, e.g., making use of the CLU system, to automatically suggest one or more medical codes based on the text of the clarification request and/or the response thereto.

Protocol

In some embodiments, a suitable protocol may be used to exchange documents and may be used to facilitate communication between a medical coding system and a CDI system. As examples, the protocol may be used to perform one or more of: determining whether new documents have arrived on the system; listing documents on the system; filtering documents according to suitable criteria; checking permissions for a user accessing the documents; filtering documents based on permissions; sending codes to the medical coding system from the CDI system; and/or other actions or steps.

In some embodiments, the protocol may be used in connection with an Application Programming Interface (API). In some embodiments, a medical coding system may make a request for a document from a CDI system or vice versa. In other embodiments, a CDI system may contact a medical coding system that is enabled to receive documents, and the CDI system may initiate the transmission of documents to the medical coding system. Documents may be sent, received, and/or requested together with, or separately from, metadata and/or other associated data, which may include codes, as well as standard file metadata such as creation date, modification date, file type, document name, document author, document creator, and/or other such data.

In some embodiments, an API may enable a medical coding system to request a listing of documents, such as clarification documents. In some embodiments, an API may enable a medical coding system to request a listing of clarification documents available in an electronic health record (EHR). In some embodiments, an API may enable a medical coding system to request the contents of a particular document. Documents may be stored at the medical coding system, at the CDI system, or at another server or storage device.

User Interface

The medical coding system may have a user interface for presenting coders with CDI clarification requests created by CDSes and represented as documents in the medical coding system. These documents may be created as hybrid documents, wherein CDI clarification information for an encounter may be rendered in a form that may be displayed to the coder. In some embodiments, this may be a graphical image format, such as a Joint Photographic Experts Group (JPEG) format or a tagged image file format (TIFF) format, or another format. In some embodiments, this may be in a Portable Document Format (PDF) format.

In some embodiments, the clarification requests may appear in the same list as other documents that are used for coding purposes. This may allow the coder to be alerted of gaps or additional documentation that may be available. Clarification requests may be shown in a document panel, along with other clinical documents, to indicate to the coder what queries have been raised about documents, prompting the coder to look for additional documents with corrections. It may also prevent the coder from submitting duplicate clarification requests. In some embodiments, the clarification requests may have been created manually. In other embodiments, the clarification requests may have been created programmatically, such as with a CLU system, or in any other suitable way. In other embodiments, some clarification requests may have been created manually and others via an automated system.

In some embodiments, clarification requests may be shown as documents at the medical coding system. In some embodiments, all documents relating to a patient may be displayed in a single window or portion of the screen. These documents may include: medical history; physical exam records; discharge summaries; emergency room records; consultation records; progress notes; operative reports; other hospital or patient care reports; and/or other documents. In some embodiments, the clarification request documents may be shown at the same level as, and/or as a peer with, other health records. Peer documents may be shown together in a list with identical or similar indentation, visual position, or text characteristics. Documents may contain headers, formatting, colors, pagination, and/or other characteristics. The clarification request may be shown using a distinct document type that identifies that the document is a clarification request, and is not a doctor health record, hospital document, or other type of document. In some embodiments, codes associated with a clarification request may be displayed in conjunction with the display of the clarification request. Documents created by a clinician in response to a clarification request may also be shown, in some embodiments in proximity to the relevant clarification request.

Figure 7G:
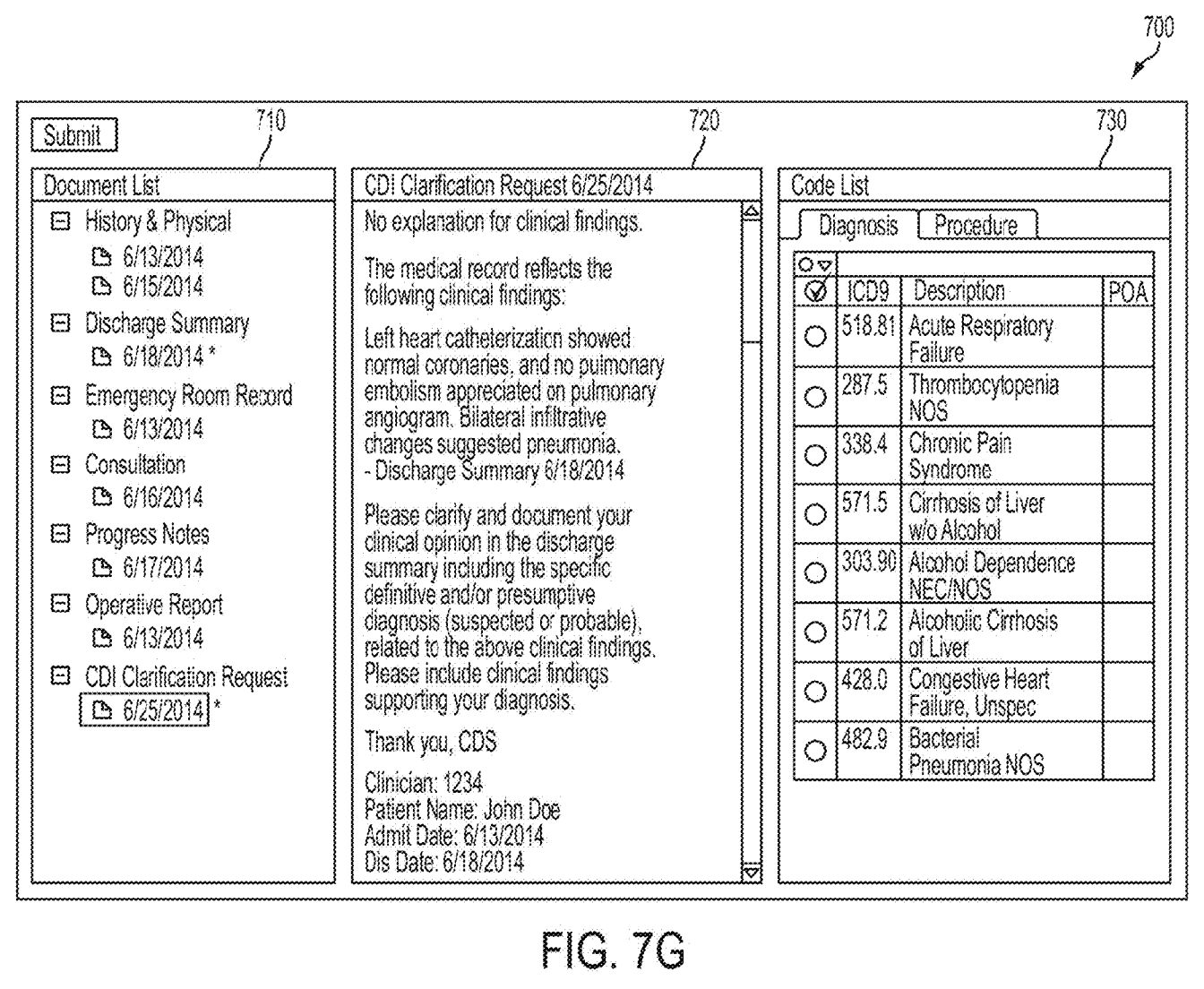

For example, FIG. 7G illustrates one possible way of displaying a CDI clarification request to a user within exemplary GUI 700 of the exemplary CAC system described above. In the example of FIG. 7G, a CDI clarification request dated Jun. 25, 2014 is listed in document list 710 as a document together with, and as a peer document with, the other documents (progress notes, discharge summary, etc.) reviewed by the coder while coding the patient encounter. When the user selects the clarification request in the document list 710, the content of the clarification request may be displayed in panel 720, where the content of any other document selected from document list 710 would likewise be displayed. In such a way, in some embodiments CDI clarification requests may be presented within the CAC system as part of the coder's normal workflow, so that the coder can seamlessly be made aware of the existence and content of clarification requests while coding the patient encounter. In some embodiments, as discussed above, a clarification request may be presented in association with one or more documents for which the clarification request was generated at the CDI system. For instance, in the example of FIG. 7G, the matching asterisks by the clarification request and the discharge summary in document list 710 provide a visual indication to the user that this particular clarification request is associated with the discharge summary (e.g., in this case, the clarification request seeks clarification of particular clinical findings set forth in the discharge summary). It should be appreciated, however, that this is merely an example, and embodiments are not limited to any such indicator.

In some embodiments, notifications and alerts may be shown to indicate the availability of documents, such as a clarification request. The notification may be an alert message presented within the user interface. A modal or modeless alert may be used. The alert may include an icon or other graphical element. The alert may be placed in the middle of the screen, near the document window or document pane, or in another position. The alert may indicate when a new document comes in, when a new clarification request has been received, or when other information is received from the CDI system. A notification may also be shown in response to receiving a notification or a document from a clinician or an electronic health record (EHR).

In some embodiments, a user can refresh the document list. In some embodiments, the document list may be automatically refreshed when a new document, such as a new clarification request or response, becomes available. Alternatively or additionally, the user interface may refresh the document list at intervals, or at every time the document list is displayed.

In some embodiments, the user interface may be displayed in a web browser or a web browser view or sub-view. In some embodiments, the user interface may be accessed remotely from a server on a private network or on a public network such as the Internet. Communication may likewise be performed over a private network or a public network such as the Internet.

Session-based connections may be used to authenticate users and keep connections alive, in some embodiments. Authentication may be performed to limit access to documents. Authentication may also be enabled to permit certain users to have permissions or privileges to access certain aspects of the user interface, such as CDI permissions and/or CAC permissions. In some embodiments, HIPAA compliance may be enabled using permissions.

Example Embodiments

Figure 11:
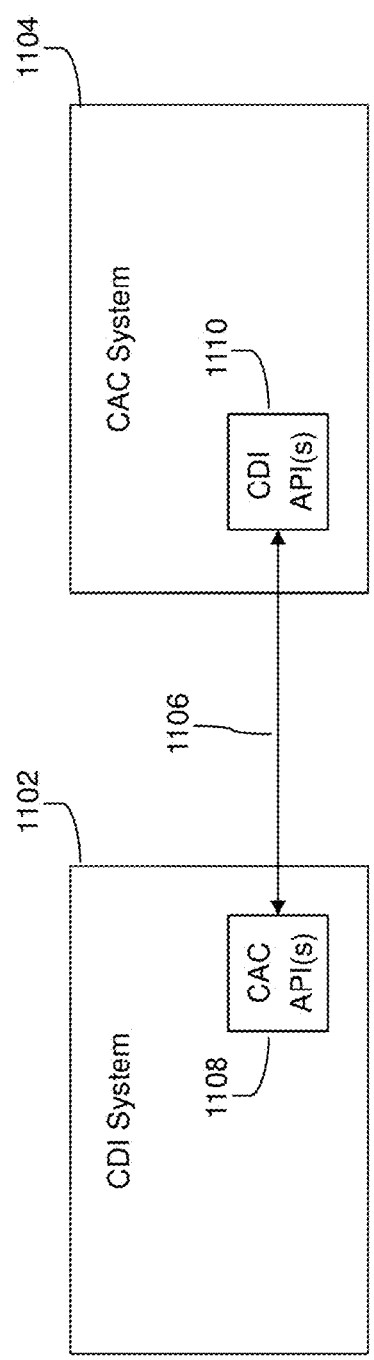
FIG. 11 illustrates an exemplary communication system between a CDI system and a CAC system in accordance with some embodiments.

FIG. 11 shows an example implementation of an architecture in which a clinical documentation improvement (CDI) system 1102, such as that described above in connection with FIG. 10, is integrated with a medical coding system, such as the CAC system 1104 described above in connection with FIG. 9, via a link 1106. In other embodiments, a manual medical coding system may be used in place of CAC system 1104.

The link 1106 may be implemented in any of numerous ways, and embodiments are not limited to any particular type of interlinking mechanism. In some embodiments, for example, the systems 1102, 1104 may communicate over a network via one or more Application Programming Interfaces (APIs) 1108, 1110, such as Web Services APIs, implemented in the software of the two systems. Such implementations may, for example, employ Simple Object Access Protocol (SOAP) messages formatted in Extensible Markup Language (XML) and sent using the Hypertext Transfer Protocol (HTTP). In other embodiments, the systems 1102, 1104 may additionally or alternatively employ Representative State Transfer (REST) to exchange messages, and the transferred data may be formatted using JavaScript Object Notation (JSON), XML, or any other suitable structured data format. In yet other embodiments, the systems 1102, 1104 may additionally or alternatively exchange messages using HTTP POST and/or GET request methods, and/or may employ APIs with traditional HTTP endpoints.

In some embodiments, upon opening of a patient case within the CDI system 1102, a call may, for example, be made to a CAC API 1108 of the CDI system 1102 to request the transfer of a structured data set for the patient from a database accessible by the CDI system 1102 to a medical coding system, such as CAC system 1104. As noted above, the structured data set may be formatted using a suitable structured data format, such as XML, BON, etc. In response to such a Web Services API call, the CAC API 1108 may send, via link 1106, a structured data set containing some or all documents or data representing clarification requests known to CDI system 1102 as of the time of the request. The structured data may be received by CDI API 1110 within CAC system 1104.

In some embodiments, a function call, may, for example, be made from a CAC system 1104 to a CDI API 1110 to request the transfer of the structured data set for the patient from a database accessible by the CDI system 1102 to the CAC system 1104. In response to such a function call, which may be a Web Services API call, the CDI API 1110 may send, via link 1106, a request to CAC API 1108 requesting the structured data set containing some or all documents or data representing clarification requests known to CDI system 1102 as of the time of the request. Upon receipt of such a request at CAC API 1108, from CDI API 1110 or from another source, CDI system 1102 may send the structured data to CAC system 1104 via CAC API 1108 and link 1106.

The interface between CDI system 1102 and CAC system 1104 thus may allow information of various types to be transmitted to the CAC system 1104, where it may be accessed and acted upon by a coder operating CAC system 1104, by an automated or semi-automated process at CAC system 1104, or by another process or user. In some embodiments, for example, the transmitted information may include information about clarification requests that were generated at CDI system 1102 and previously forwarded to the clinician for review. Upon transmission of the information to the CAC system 1104, the information may be displayed in a user interface to a coder, who may then be enabled to use the information in conjunction with other medical record information to more accurately assign medical billing codes to the medical record.

As noted above, in some embodiments, the CAC system 1104 may display the received information in the general format of other medical record documents displayed by CAC system 1104, such that the coder need only use a single interface to perform coding tasks while being enabled to access information from various sources, e.g., from a medical documentation system, and/or from the CDI system 1102. In some embodiments, the clarification requests received from the different sources may be identified and/or displayed by CAC system 1104 in different ways, such as by highlighting the requests received from the respective sources using different colors and/or displaying the requests in different locations on the screen. In some embodiments, the clarification requests may be displayed in a document display area or document list pane on the screen.

In some embodiments, some or all state changes and/or events that occur with respect to clarification requests maintained by or accessible to CDI system 1102 may be automatically communicated to CAC system 1104 by CDI system 1102 making a call to CDI API 1110 of CAC system 1104. For example, when CDI system 1102 sends a clarification request to a clinician, CDI system 1102 may also make a call to CDI API 1110 of CAC system 1104 to communicate the occurrence of such an event and/or record update to CAC system 1104. In some embodiments, this communication step may occur substantially simultaneously with the occurrence of the event and/or record update. As another example, when a clinician responds to a clarification request and updates a record using a medical documentation system, the medical documentation system may communicate the occurrence of such an event and/or record update to CDI system 1102, which then may send a record update to CAC system 1104. Corresponding patient specific records of the CDI system 1102, e.g., records stored in a database, can thus be updated accordingly to reflect such events and/or record updates. In other embodiments, the medical documentation system may additionally or alternatively automatically push information to the CDI system 1102 using some other suitable technique, such as an HTTP POST request method, so as to ensure that the CDI system 1102 has access to up-to-date audit information from the documentation management system. Such updates may, for example, be communicated periodically and/or in response to detected state changes in the data maintained by the medical documentation system.

Figure 12:
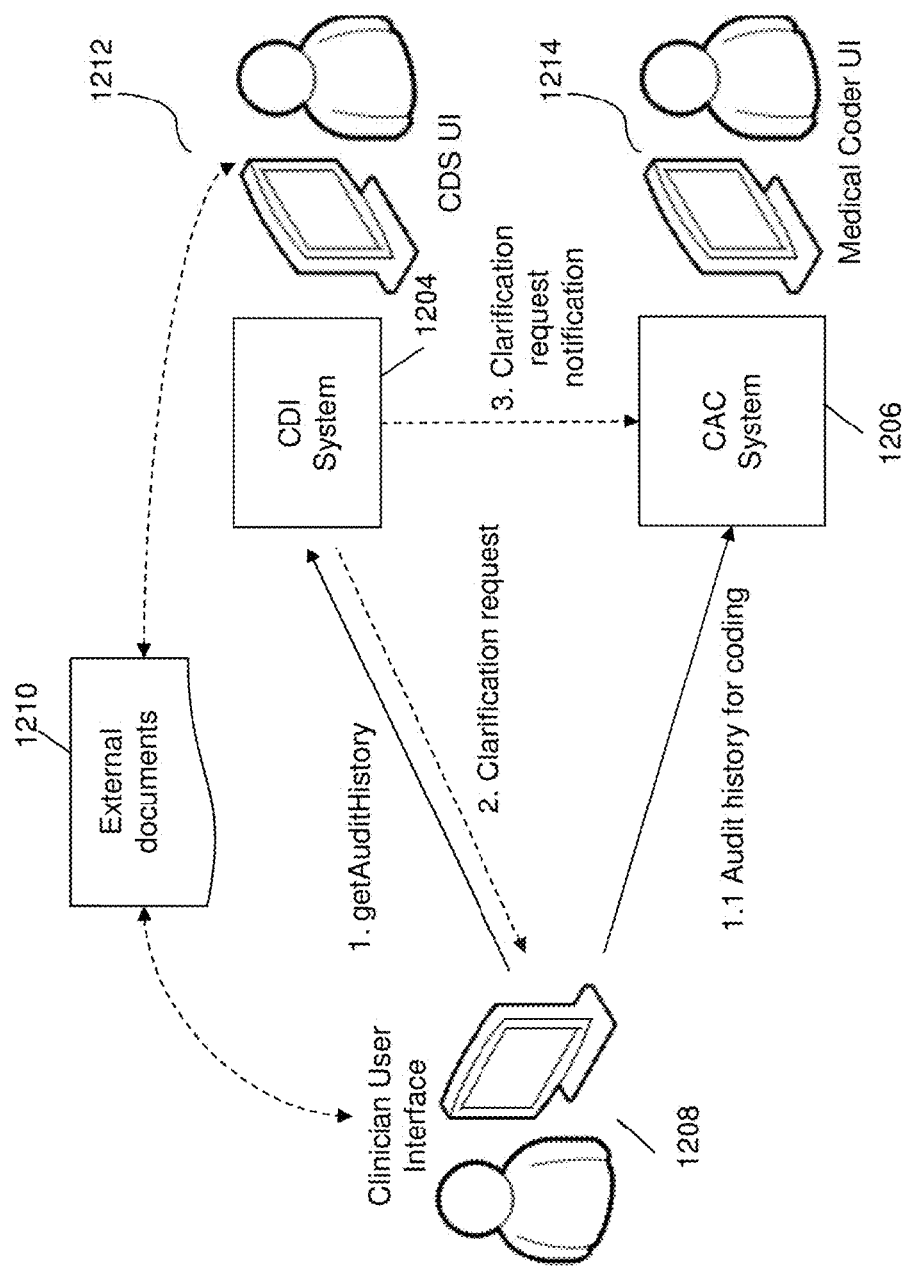
FIG. 12 illustrates an exemplary interaction involving a CDI system and a CAC system in accordance with some embodiments.

FIG. 12 illustrates an exemplary workflow in which the interface between a CDI system 1204 and a CAC system 1206 may be exploited to achieve certain benefits. In some embodiments, a CDS may interact with the CDI system 1204, and a clinician may interact with a clinician user interface 1208 in any of the ways and for any of the purposes discussed above. In some embodiments, a medical coder may interact with the CAC system 1206, which may be in communication with both CDI system 1204 and the clinician user interface 1208.

In some embodiments, the clinician user interface 1208 may be a user interface such as the user interface 110 shown in FIG. 1. The clinician may, for example, use system 100 to create and/or modify one or more medical records for storage in an EHR system, which may, for example, include the patient history records database 160 discussed above in connection with FIG. 1.

In some embodiments, the CDS may operate a user interface 1212, which may be a user interface such as the user interface 1014 shown in FIG. 10, The CDS may also access the EHR system so as to review one or more records for a particular patient as a part of the CDI process. As shown, the CDS may, in some embodiments, also have access to other external documents 1210 also accessible to the clinician, which may, for example, include laboratory records, handwritten clinician notes, etc., that are not received by or considered by the CLU system 100.

In some embodiments, the coder may operate a user interface 1214 at CAC system 1206, which may be a CAC user interface such as the user interface 914 shown in FIG. 9. The coder may review information received from the clinician user interface, one or more personal health records, and/or the CDI system for performing medical coding, in some embodiments. In some embodiments, the CAC system 1206 may request an audit history for coding from the clinician or the EHR system, as depicted in FIG. 12. The clinician or EHR system may provide in response the documents needed for the coding specialist to perform coding.

As shown in FIG. 12, in some embodiments, upon the CDS creating and/or accessing a patient specific record using the CDI system 1204, the CDI system 1204 may make a call to a "getAuditHistory" API on the medical documentation system. In response to such an API call, the medical documentation system may transmit a structured data set for the patient to the CDI system 1204. The CDS may then be able to use the transmitted data reflecting some or all of the activity of the medical documentation system relating to the patient for the purpose of formulating new clarification requests to be communicated to the clinician based on the data and/or to refrain from making clarification requests that have already been asked and responded to by the clinician. New clarification requests may be communicated from the CDS to the clinician in any suitable way, including any of the conventional techniques noted above, and including via a call to an API on the medical documentation system. In some embodiments, a "getAuditHistory" API may not be required, and a manual request for documents, followed by a manual review of one or more patient history documents, may be performed by a CDS, with or without a CDS UI 1212. In some embodiments, a request may be made by CDI system 1204 for the documents, i.e., the "getAuditHistory" request. In other embodiments, the documents may automatically be sent to the CDI system without a prior request.

In some embodiments, the CDS interfacing with the CDI system 1204 may wish to formulate and communicate new clarification requests to the clinician. Such new clarification requests may, for example, be based upon the structured data set for a patient received from the medical documentation system, or may additionally or alternatively be based upon one or more records accessed from an EHR system, and/or one or more external documents 1210. In some embodiments, CDI system 1204 may, allow such new clarification requests formulated by the CDS to be communicated to the medical documentation system, so as to cause them to be communicated to the clinician. In some embodiments, such new clarification requests may be communicated to the medial documentation system by calling a "submitClarificationRequest" API on the medical documentation system.

In some embodiments, CDI system 1204 may communicate clarification requests to a medical coding system, in addition to communicating the clarification requests to the clinician. Such clarification requests may be the same clarification requests sent to the clinician. In such instances, a clarification request notification may be sent from CDI system 1204 to CAC system 1206 using one or more protocols and/or APIs, as described elsewhere herein. In some embodiments, the clarification request notification may be sent by the CDI system 1204 absent any request from the CAC system 1206. In other embodiments, a request from CAC system 1206 may initiate the transmission of the clarification request notification from CDI system 1204 to CAC system 1206. In some embodiments, clarification request notifications may be notifications accompanied by one or more documents pertaining to the clarification request sent to the clinician. In some embodiments, clarification request notifications may be sent subsequent to, or substantially simultaneously with, the transmission of clarification requests from CDI system 1204 to the clinician.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing", "involving", and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A Clinical Document Improvement (CDI) system that generates a clarification request for resolution by a clinician, the CDI system comprising:
   at least one processor; and
   at least one computer-readable medium comprising processor-executable instructions, which when executed by the at least one processor, cause the at least one processor to perform a method comprising:
      in response to generating the clarification request relating to at least one medical document relating to a patient encounter between a patient and the clinician, the clarification request requesting that the clinician provide additional information regarding the at least one medical document:
         transmitting, from the CDI system to a Computer-Assisted Coding (CAC) system, a notification of the clarification request, for presentation to a medical coder via a user interface at the CAC system in association with the at least one medical document for which the clarification request was generated at the CDI system, wherein the CAC system generates one or more medical codes associated with the at least one medical document, and presents, via the user interface, the one or more medical codes and the at least one medical document for which the one or more medical codes were generated to the medical coder; and
      after receiving, at the CDI system, a response of the clinician to the clarification request:
         subsequent to transmitting the notification of the clarification request from the CDI system to the CAC system, transmitting, from the CDI system to the CAC system, the response of the clinician to the clarification request.

2. The system of claim 1, wherein the notification of the clarification request includes the notification and one or more documents pertaining to the clarification request.

3. The system of claim 1, wherein the method further comprises:
   transmitting to the CAC system, from the CDI system, identification of the at least one medical document for which the clarification request was generated.

4. The system of claim 1, wherein the method further comprises:
   transmitting to the CAC system, from the CDI system, identification of at least one medical billing code for which the clarification request was generated.

5. The system of claim 1, wherein transmitting a notification comprises transmitting the notification via an Application Programming Interface (API) of the CDI system.

6. The system of claim 5, wherein the method further comprises:
   communicating documents representing clarification requests via the API.

7. A Computer-Assisted Coding (CAC) system that generates one or more medical codes associated with at least one medical document relating to a patient encounter between a patient and a clinician and presents, via a user interface, the one or more medical codes and the at least one medical document to a medical coder, the CAC system comprising:
   at least one processor; and
   at least one computer-readable medium comprising processor-executable instructions, which when executed by the at least one processor, cause the at least one processor to perform a method comprising:
      receiving, at the CAC system from a Clinical Document Improvement (CDI) system, a notification of a clarification request generated at the CDI system for resolution by the clinician, the clarification request relating to the at least one medical document and requesting that the clinician provide additional information regarding the at least one medical document;
      presenting, to the medical coder and via the user interface at the CAC system, the notification of the clarification request in association with the at least one medical document for which the clarification request was generated at the CDI system; and subsequent to receiving the notification of the clarification request at the CAC system from the CDI system, receiving, at the CAC system from the CDI system, a response of the clinician to the clarification request.

8. The system of claim 7, wherein the method further comprises presenting to the medical coder, at the CAC system, a visual indication that the clarification request is associated with the at least one medical document for which the clarification request was generated at the CDI system.

9. The system of claim 7, wherein the method further comprises presenting to the medical coder, at the CAC system, the notification of the clarification request in association with at least one medical billing code for which the clarification request was generated at the CDI system.

10. The system of claim 7, wherein the method further comprises presenting to the medical coder, at the CAC system, the clarification request as a peer document with the at least one medical document for the patient encounter for which the clarification request was generated at the CDI system.

11. The system of claim 7, wherein the method further comprises suppressing generation and/or transmission, at the CAC system, of a duplicate clarification request matching the clarification request generated at the CDI system.

12. The system of claim 7, wherein the notification of the clarification request includes the notification and one or more documents pertaining to the clarification request, and the method further comprises:
analyzing, at the CAC system, the one or more documents pertaining to the clarification request to automatically suggest the one or more medical codes for the patient encounter.

13. The system of claim 7, wherein the method further comprises presenting to the medical coder, at the CAC system, the clinician's response as a peer document with the clarification request and the at least one medical document for the patient encounter for which the clarification request was generated at the CDI system.

14. The system of claim 7, wherein the method further comprises analyzing, at the CAC system, the clinician's response to automatically suggest one or more additional medical codes based on text of the clinician's response.

15. At least one non-transitory computer-readable storage medium storing computer-executable instructions that, when executed, perform a method for use with a Clinical Document Improvement (CDI) system implemented via at least one processor and generating a clarification request for resolution by a clinician, the CDI system configured to communicate with a Computer-Assisted Coding (CAC) system that analyzes at least one medical document, generates one or more medical codes associated with the at least one medical document, and presents, via a user interface, the one or more medical codes and the at least one medical document for which the one or more medical codes were generated to a medical coder, the method comprising:
in response to generating, at the CDI system, a clarification request relating to the at least one medical document relating to a patient encounter between a patient and the clinician, the clarification request requesting that the clinician provide additional information regarding the at least one medical document;
transmitting, from the CDI system to the CAC system, a notification of the clarification request, for presentation to the medical coder via the user interface at the CAC system in association with the at least one medical document for which the clarification request was generated at the CDI system; and
after receiving, at the CDI system, a response of the clinician to the clarification request:
subsequent to transmitting the notification of the clarification request from the CDI system to the CAC system, transmitting, from the CDI system to the CAC system, the response of the clinician to the clarification request.

16. The at least one non-transitory computer-readable storage medium of claim 15, wherein the notification of the clarification request includes the notification and one or more documents pertaining to the clarification request.

17. The at least one non-transitory computer-readable storage medium of claim 15, wherein the method further comprises transmitting to the CAC system, from the CDI system, identification of the at least one medical document for which the clarification request was generated.

18. The at least one non-transitory computer-readable storage medium of claim 15, wherein the method further comprises transmitting to the CAC system, from the CDI system, identification of at least one medical billing code for which the clarification request was generated.

19. The at least one non-transitory computer-readable storage medium of claim 15, wherein transmitting a notification comprises transmitting the notification via an Application Programming Interface (API) of the CDI system.

20. The at least one non-transitory computer-readable storage medium of claim 19, wherein the method further comprises:
communicating documents representing clarification requests via the APL.

* * * * *